US006022950A

United States Patent [19]

Murphy

[11] Patent Number: 6,022,950

[45] Date of Patent: Feb. 8, 2000

[54] HYBRID MOLECULES HAVING TRANSLOCATION REGION AND CELL-BINDING REGION

[75] Inventor: John R. Murphy, Boston, Mass.

[73] Assignee: Seragen, Inc., Hopkinton, Mass.

[21] Appl. No.: 08/479,510

[22] Filed: Jun. 7, 1995

Related U.S. Application Data

[63] Continuation-in-part of application No. 08/102,387, Aug. 4, 1993, Pat. No. 5,668,255, which is a continuation of application No. 07/722,484, Jun. 27, 1991, abandoned, which is a continuation-in-part of application No. 07/538,276, Jun. 14, 1990, abandoned, which is a continuation-in-part of application No. 07/456,095, Dec. 22, 1989, abandoned, which is a continuation-in-part of application No. 06/742,554, Jun. 7, 1985, abandoned, which is a continuation-in-part of application No. 06/726,808, Apr. 25, 1985, abandoned, which is a continuation of application No. 06/618,199, Jun. 7, 1984, abandoned.

[51] Int. Cl.[7] .......................... C07K 14/00; C07K 14/485; C07K 14/55; C07K 16/28

[52] U.S. Cl. ...................... 530/350; 530/351; 530/387.3; 530/388.1

[58] Field of Search .................................... 530/324, 350, 530/402, 387.3, 388.1, 351

[56] References Cited

U.S. PATENT DOCUMENTS

| | | | |
|---|---|---|---|
| 4,336,336 | 6/1982 | Silhavy et al. | 435/6 |
| 4,350,764 | 9/1982 | Baxter et al. | 435/69.4 |
| 4,366,246 | 12/1982 | Riggs | 435/69.8 |
| 4,425,437 | 1/1984 | Riggs | 435/320.1 |
| 4,468,382 | 8/1984 | Bacha et al. | 514/19 |
| 4,469,631 | 9/1984 | Baxter et al. | 530/302 |
| 4,479,940 | 10/1984 | Bizzini | 514/773 |
| 4,520,011 | 5/1985 | Neville, Jr. | 424/182.1 |
| 4,532,207 | 7/1985 | Brewer et al. | 435/69.4 |
| 4,543,329 | 9/1985 | Daum et al. | 435/69.1 |
| 4,545,985 | 10/1985 | Pastan et al. | 424/180.1 |
| 4,546,082 | 10/1985 | Kurian et al. | 435/6 |
| 4,563,424 | 1/1986 | Riggs | 435/69.4 |
| 4,594,336 | 6/1986 | Bizzini | 514/2 |
| 4,666,837 | 5/1987 | Harford et al. | 435/69.3 |
| 4,675,382 | 6/1987 | Murphy | 530/350 |
| 5,080,898 | 1/1992 | Murphy | 424/94.1 |
| 5,135,736 | 8/1992 | Anderson et al. | 424/1.49 |
| 5,169,933 | 12/1992 | Anderson et al. | 530/391.3 |
| 5,328,984 | 7/1994 | Pastan et al. | 424/134.1 |

FOREIGN PATENT DOCUMENTS

| | | |
|---|---|---|
| 0012078 | 6/1980 | European Pat. Off. . |
| 0261671 | 3/1988 | European Pat. Off. . |
| 4104186 A1 | 8/1992 | Germany . |
| 4115038 A1 | 11/1992 | Germany . |
| 2091268 | 7/1982 | United Kingdom . |
| 2091269 | 7/1982 | United Kingdom . |
| 8000030 | 1/1980 | WIPO . |
| 9004414 | 5/1990 | WIPO . |
| 91-09871 | 7/1991 | WIPO . |

OTHER PUBLICATIONS

Bacha, et al., Endocrinology 113(3):1072–76 (1983).
Bacha, et al., J. Biol. Chem. 258(3):1565–70 (1983).
Greenfield, et al., Proc. Nat'l. Acad. Sci. USA 80(22):6853–57 (1983).
Kaczorek, et al., Science 221:855–58 (1983).
Leong, et al., Science 220:515–17 (1983).
Itakura, et al., Science 198:1057–63 (1977).
Blythman, et al., Nature 290:145–6 (1981).
Roth, et al., J. Cell. Physiol. 115(2):151–8 (1983).
Roth, et al., J. Biol. Chem. 256(11):5350–5354 (1981).
Reichlin, et al., Proc. Am. Pept. Symp., 8th, Hruby, V. et al. (eds.), Pierce Chem. Co., Rockford, Ill. (1983),pp. 837–852.
Miskimins, et al., Biochem. Biophys. Res. Comm. 91:143–51 (1979).
Cawley, et al., Cell 22:563–70 (1980).
Villa–Komaroff, et al., Proc. Nat'l. Acad. Sci. USA 75:3727–31 (1978).
Chang, et al., J. Biol. Chem. 252:1515–22 (1977).
Oeltman, et al., J. Biol. Chem. 254:1028–32 (1979).
Bird, et al., Science 242:423–6 (1988).
Calderwood, et al., Proc. Nat'l. Acad. Sci. USA 84:4364–68 (1987).
Youle, et al., J. Biol. Chem. 254:11089–11096 (1979).
Poznansky, et al., Science 223:1304–1306 (1984).
Sundan, et al., J. Biol. Chem. 257:9733–39 (1982).
Uchida, et al., J. Biol. Chem. 255:6687–93 (1980).
Neville, et al., Immunological Review 62:75–91 (1982).
Gilliland, et al., J. Biol. Chem. 256:12731–39 (1981).
Gilliland, et al., Proc. Nat'l. Acad. Sci. USA 77:4539–43 (1980).
Oeltmann, et al., Arch. Biochem. Biophys. 209:362–70 (1981).

(List continued on next page.)

*Primary Examiner*—Nancy Degen
*Assistant Examiner*—Robert Schwartzman
*Attorney, Agent, or Firm*—Lerner, David, Littenberg, Krumholz & Mentlik, LLP

[57] ABSTRACT

Disclosed is a hybrid molecule comprising a first part, a second part, and a third part connected by covalent bonds, (a) wherein said first part comprises a portion of the binding domain of a cell-binding polypeptide ligand effective to cause said hybrid protein to bind to a cell of an animal;

(b) wherein said second part comprises a portion of a translocation domain of naturally occurring protein which translocates said third part across the cytoplasmic membrane into the cytosol of the cell; and (c) wherein said third part comprises a chemical entity to be introduced into the cell, wherein each of said first part and said third part is non-native with respect to said naturally occurring protein, and further wherein said covalent bond connecting said second part and said third part is a cleavable bond, provided that when said second part comprises a portion of a translocation domain of Pseudomonas exotoxin, said third part is not a polypeptide.

51 Claims, 19 Drawing Sheets

OTHER PUBLICATIONS

Uchida, et al., Biochem. Biophys. Res. Comm. 87:268–73 (1978).
Bishai, et al., J. Bacteriol. 169:5140–51 (1987).
Williams, et al., J. Biol. Chem. 265:20673–77 (1990).
O'Hare, et al., FEBS Lett. 273:200–04 (1990).
Hoch, et al., Proc. Nat'l. Acad. Sci. USA 82:1692–96 (1985).
Bizzini, et al., J. Neurochem. 28:529–42 (1977).
Chaudhary, et al., Nature 339:394–97 (1988).
Deleers, et al., FEBS 160:82–86 (1983).
Hwang, et al., Cell 48:129–136 (1987).
Gray, et al., Proc. Nat'l. Acad. Sci. USA 81:2645–2649 (1984).
Government Reports From Information on Demand, Inc., Report No. PB88–238431, "Vector for Secretion of Proteins Directly Into Periplasm or Culture Medium".
Rosenberg, Science, 223:1412–1415 (1984).
Chen et al., Gene Therapy 2:116–123 (1995).
Johnston et al. (1993) Present status and future prospects for HIV therapies. Science 260:1286–1293, May 1993.

FRAGMENT A'
FRAGMENT B'
Sau 3AI
Nsi I
Sph I
α-MSH
EcoRI
pABM508
Hind III
Nsi I
+
Sph I
1/2 Nsi I
1/2 Sph I
LINKERS
Nco I
1/2 Nsi I
STICKY
END
+
1/2 Sph I
1/2 Hind III
FRAGMENT B'
Nco I
Nsi I
Sph I
1/2 HindIII
STICKY
END
EcoRI
Nco I
BamHI
Pst I
HindIII
SalI
Ptrc
pKK233-2
Hind III
+
Nco I
Ptrc
1/2 Hind III
Sal I
EcoRI
1/2 Nco I
BamHI
FRAGMENT B'
Sph I
Nsi I
Hind III
(Nco I)
EcoRI
BamHI
Ptrc
Sal I

FIG. 5A

```
        10         20         30         40         50         60
         |          |          |          |          |          |
ATGGTAAAGATAATATTTGTGTTTTTTATTTTCTTATCATCATTTTCATATGCAAATGAT
METValLysIleIlePheValPhePheIlePheLeuSerSerPheSerTyrAlaAsnAsp

        70         80  XbaI   90        100        110        120
         |          |          |          |          |          |
GATAAGTTATATCGGGCAGATTCTAGACCTCCTGATGAAATAAAGCAGTCAGGTGGTCTT
AspLysLeuTyrArgAlaAspSerArgProProAspGluIleLysGlnSerGlyGlyLeu

       130        140        150        160        170        180
         |          |          |          |          |          |
ATGCCAAGAGGACAGAGTCAGTACTTTGACCGAGGTACTCAAATGAATATCAACCTTTAT
METProArgGlyGlnSerGlnTyrPheAspArgGlyThrGlnMETAsnIleAsnLeuTyr

       190        200        210        220        230        240
         |          |          |          |          |          |
GATCATGCAAGAGGAACTCAGACGGGATTTGTTAGGCACGATGATGGATATGTTTCCACC
AspHisAlaArgGlyThrGlnThrGlyPheValArgHisAspAspGlyTyrValSerThr

       250        260        270        280        290        300
         |          |          |          |          |          |
TCAATTAGTTTGAGAAGTGCCCACTTAGTGGGTCAAACTATATTGTCTGGTCATTCTACT
SerIleSerLeuArgSerAlaHisLeuValGlyGlnThrIleLeuSerGlyHisSerThr

       310        320        330        340        350        360
         |          |          |          |          |          |
TATTATATATATGTTATAGCCACTGCACCCAACATGTTTAACGTTAATGATGTATTAGGG
TyrTyrIleTyrValIleAlaThrAlaProAsnMETPheAsnValAsnAspValLeuAla

       370        380        390        400        410        420
         |          |          |          |          |          |
GCATACAGTCCTCATCCAGATGAACAAGAAGTTTCTGCTTTAGGTGGGATTCCATACTCC
AlaTyrSerProHisProAspGluGlnGluValSerAlaLeuGlyGlyIleProTyrSer
```

FIG. 5B

```
         430        440        450        460        470        480
CAAATATATGGATGGTATCGAGTTCATTTTGGGGTGCTTGATGAACAATTACATCGTAAT
GlnIleTyrGlyTrpTyrArgValHisPheGlyValLeuAspGluGlnLeuHisArgAsn

         490        500        510        520        530        540
AGGGGCTACAGAGATAGATATTACAGTAACTTAGATATTGCTCCAGCAGCAGATGGTTAT
ArgGlyTyrArgAspArgTyrTyrSerAsnLeuAspIleAlaProAlaAlaAspGlyTyr

         550        560        570        580        590        600
GGATTGGCAGGTTTCCCTCCGGAGCATAGAGCTTGGAGGGAAGAGCCGTGGATTCATCAT
GlyLeuAlaGlyPheProProGluHisArgAlaTrpArgGluGluProTrpIleHisHis

      Scr FI
         610        620        630        640        650        660
GCACCGCCGGGTTGTGGGAATGCTCCAAGATCATCGATGAGTAATACTTGCGATGAAAAA
AlaProProGlyCysAlaAsnAlaProArgSerSerMETSerAsnThrCysAspGluLys

         670        680        690        700        710        720
ACCCAAAGTCTAGGTGTAAAATTCCTTGACGAATACCAATCTAAAGTTAAAAGACAAATA
ThrGlnSerLeuGlyValLysPheLeuAspGluTyrGlnSerLysValLysArgGlnIle

         730        740        750        760        770  STOP  780
TTTTCAGGCTATCAATCTGATATTGATACACATAATAGAATTAAGGATGAATTATGATTA
PheSerGlyTyrGlnSerAspIleAspThrHisAsnArgIleLysAspGluLeu---Leu
```

FIG. 8A

```
          10        20        30        40        50        60
ATGAAAATAATTATTTTTAGAGTGCTAACTTTTTTCTTTGTTATCTTTTCAGTTAATGTG
METLysIleIleIlePheArgValLeuThrPhePhePheValIlePheSerValAsnVal

          70        80    TaqI 90       100       110       120
GTGGCGAAGGAATTTACCTTAGACTTCTCGACTGCAAAGACGTATGTAGATTCGCTGAAT
ValAlaLysGluPheThrLeuAspPheSerThrAlaLysThrTyrValAspSerLeuAsn

         130       140       150       160       170       180
GTCATTCGCTCTGCAATAGGTACTCCATTACAGACTATTTCATCAGGAGGTACGTCTTTA
ValIleArgSerAlaIleGlyThrProLeuGlnThrIleSerSerGlyGlyThrSerLeu

         190       200       210       220       230       240
CTGATGATTGATAGTGGCTCAGGGGATAATTTGTTTGCAGTTGATGTCAGAGGGATAGAT
LeuMETIleAspSerGlySerGlyAspAsnLeuPheAlaValAspValArgGlyIleAsp

         250       260       270       280       290       300
CCAGAGGAAGGGCGGTTTAATAATCTACGGCTTATTGTTGAACGAAATAATTTATATGTG
ProGluGluGlyArgPheAsnAsnLeuArgLeuIleValGluArgAsnAsnLeuTyrVal

         310       320       330       340       350       360
ACAGGATTTGTTAACAGGACAAATAATGTTTTTTATCGCTTTGCTGATTTTTCACATGTT
ThrGlyPheValAsnArgThrAsnAsnValPheTyrArgPheAlaAspPheSerHisVal

         370       380       390       400       410       420
ACCTTTCCAGGTACAACAGCGGTTACATTGTCTGGTGACAGTAGCTATACCACGTTACAG
ThrPheProGlyThrThrAlaValThrLeuSerGlyAspSerSerTyrThrThrLeuGln
```

FIG. 8B

```
        430       440       450       460       470       480
CGTGTTGCAGGGATCAGTCGTACGGGGATGCAGATAAATCGCCATTCGTTGACTACTTCT
ArgValAlaGlyIleSerArgThrGlyMETGlnIleAsnArgHisSerLeuThrThrSer

        490       500       510       520       530       540
TATCTGGATTTAATGTCGCATAGTGGAACCTCACTGACGCAGTCTGTGGCAAGAGCGATG
TyrLeuAspLeuMETSerHisSerGlyThrSerLeuThrGlnSerValAlaArgAlaMET

        550       560       570       580       590       600
TTACGGTTTGTTACTGTGACAGCTGAAGCTTTACGTTTTCGGCAAATACAGAGGGGATTT
LeuArgPheValThrValThrAlaGluAlaLeuArgPheArgGlnIleGlnArgGlyPhe

        610       620       630       640       650       660
CGTACAACACTGGATGATCTCAGTGGGCGTTCTTATGTAATGACTGCTGAAGATGTTGAT
ArgThrThrLeuAspAspLeuSerGlyArgSerTyrValMETThrAlaGluAspValAsp

        670       680       690       700       710       720
CTTACATTGAACTGGGGAAGGTTGAGTAGCGTCCTGCCTGACTATCATGGACAAGACTCT
LeuThrLeuAsnTrpGlyArgLeuSerSerValLeuProAspTyrHisGlyGlnAspSer

              XmnI
        730       740       750       760       770       780
GTTCGTGTAGGAAGAATTTCTTTTGGAAGCATTAATGCAATTCTGGGAAGCGTGGCATTA
ValArgValGlyArgIleSerPheGlySerIleAsnAlaIleLeuGlySerValAlaLeu

                     Nsi
        790       800       810       820       830       840
ATACTGAATTGTCATCATCATGCATCGCGAGTTGCCAGAATGGCATCTGATGAGTTTCCT
IleLeuAsnCysHisHisHisAlaSerArgValAlaArgMETAlaSerAspGluPhePro
```

*FIG. 8C*

```
       850       860       870       880       890       900
TCTATGTGTCCGGCAGATGGAAGAGTCCGTGGGATTACGCACAATAAAATATTGTTGTGG
SerMETCysProAlaAspGlyArgValArgGlyIleThrHisAsnLysIleLeuLeuTrp

       910       920       930       940       950       960
GATTCATCCACTCTGGGGGCAATTCTGATGCGCAGAACTATTAGCAGTTGAGGGGGTAAA
AspSerSerThrLeuGlyAlaIleLeuMETArgArgThrIleSerSer---GlyGlyLys

       970       980       990      1000      1010      1020
ATGAAAAAAACATTATTAATAGCTGCATCGCTTTCATTTTTTTCAGCAAGTGCGCTGGCG
METLysLysThrLeuLeuIleAlaAlaSerLeuSerPhePheSerAlaSerAlaLeuAla

      1030      1040      1050      1060      1070      1080
ACGCCTGATTGTGTAACTGGAAAGGTGGAGTATACAAAATATAATGATGACGATACCTTT
ThrProAspCysValThrGlyLysValGluTyrThrLysTyrAsnAspAspAspThrPhe

      1090      1100      1110      1120      1130      1140
ACAGTTAAAGTGGGTGATAAAGAATTATTTACCAACAGATGGAATCTTCAGTCTCTTCTT
ThrValLysValGlyAspLysGluLeuPheThrAsnArgTrpAsnLeuGlnSerLeuLeu

      1150      1160      1170      1180      1190      1200
CTCAGTGCGCAAATTACGGGGATGACTGTAACCATTAAAACTAATGCCTGTCATAATGGA
LeuSerAlaGlnIleThrGlyMETThrValThrIleLysThrAsnAlaCysHisAsnGly

      1210      1220      1230
GGGGGATTCAGCGAAGTTATTTTTCGTTGA
GlyGlyPheSerGluValIlePheArg---
```

FIG. 11A

```
1
TCGACATTATATGATTTTAAATCAATTCCGTTTCTAATTTATAATTATTTCGTTAAACCAATCAA
66
TTCCCTTTAAACACTGCTTATGCATATTCTGTCTCAATTTATATATGGCATTGCATTCTTCCGTAT
132
TAATTTATAAGTTCACTTTTTATTGATCAAGTATTTGTGGTTTTCTTTATATAAAAAAATGTATTA
198
GTGTTTTTCTGTATTAATTTTATAAGTTCATCTTTATGAGAATGCTAATGTATTTGGACAGCCAAT
264
                              M  K  P  G  G  N  T  I  V  I  W  M  Y
AAAATTCCAGAATTGCTGCAATCAAGGATGAAACCGGGAGGAAATACTATTGTAATATGGATGTAT
330                            Signal Peptide
A  V  A  T  W  L  C  F  G  S  T  S  G  W  S  F  T  L  E  D  N  N
GCAGTGGCAACATGGCTTTGTTTTGGATCCACCTCAGGGTGGTCTTTCACATTAGAGGATAACAAC
396                                                    Signal Peptide
I  F  P  K  Q  Y  P  I  I  N  F  T  T  A  G  A  T  V  Q  S  Y  T
ATATTCCCCAAACAATACCCAATTATAAACTTTACCACAGCGGGTGCCACTGTGCAAAGCTACACA
A-chain                                       Bam I
N  F  I  R  A  V  R  G  R  L  T  T  G  A  D  V  R  H  E  I  P  V
AACTTTATCAGAGCTGTTCGCGGTCGTTTAACAACTGGAGCTGATGTGAGACATGAAATACCAGTG
519
L  P  N  R  V  G  L  P  I  N  Q  R  F  I  L  V  E  L  S  N  H  A
TTGCCAAACAGAGTTGGTTTGCCTATAAACCAACGGTTTATTTTAGTTGAACTCTCAAATCATGCA
594
E  L  S  V  T  L  A  L  D  V  T  N  A  Y  V  V  G  Y  R  A  G  N
GAGCTTTCTGTTACATTAGCGCTGGATGTCACCAATGCATATGTGGTCGGCTACCGTGCTGGAAAT
660
S  A  Y  F  F  H  P  D  N  Q  E  D  A  E  A  I  T  H  L  F  T  D
AGCGCATATTTCTTTCATCCTGACAATCAGGAAGATGCAGAAGCAATCACTCATCTTTTCACTGAT
726
V  Q  N  R  Y  T  F  A  F  G  G  N  Y  D  R  L  E  Q  L  A  G  N
GTTCAAAATCGATATACATTCGCCTTTGGTGGTAATTATGATAGACTTGAACAACTTGCTGGTAAT
792
L  R  E  N  I  E  L  G  N  G  P  L  E  E  A  I  S  A  L  Y  Y  Y
CTGAGAGAAAATATCGAGTTGGGAAATGGTCCACTAGAGGAGGCTATCTCAGCGCTTTATTATTAC
858
S  T  G  G  T  Q  L  P  T  L  A  R  S  F  I  I  C  I  Q  M  I  S
AGTACTGGTGGCACTCAGCTTCCAACTCTGGCTCGTTCCTTTATAATTTGCATCCAAATGATTTCA
924                                   Fsp I
E  A  A  R  F  Q  Y  I  E  G  E  M  R  T  R  I  R  Y  N  R  R  S
GAAGCAGCAAGATTCCAATATATTGAGGGAGAAATGCGCACGAGAATTAGGTACAACCGGAGATCT
990
A  P  D  P  S  V  I  T  L  E  N  S  W  G  R  L  S  T  A  I  Q  E
GCACCAGATCCTAGCGTAATTACACTTGAGAATAGTTGGGGGAGACTTTCAACTGCAATTCAAGAG
1056
S  N  Q  G  A  F  A  S  P  I  Q  L  Q  R  R  N  G  S  K  F  S  V
TCTAACCAAGGAGCCTTTGCTAGTCCAATTCAACTGCAAAGACGTAATGGTTCCAAATTCAGTGTG
1122                                                 Fsp I
Y  D  V  S  I  L  I  P  I  I  A  L  M  V  Y  R  C  A  P  P  P  S
TACGATGTGAGTATATTAATCCCTATCATAGCTCTCATGGTGTATAGATGCGCACCTCCACCATCG
```

FIG. 11B

```
1188                                           Bam I
S  Q  F  S  L  L  I  R  P  V  V  P  N  F  N  A  D  V  C  M  D  P
TCACAGTTTTCTTTGCTTATAAGGCCAGTGGTACCAAATTTTAATGCTGATGTTTGTATGGATCCT
 A-chain| Linker Peptide                           |B-chain
1254
E  P  I  V  R  I  V  G  R  N  G  L  C  V  D  V  R  D  G  R  F  H
GAGCCCATAGTGCGTATCGTAGGTCGAAATGGTCTATGTGTTGATGTTAGGGATGGAAGATTCCAC
1320
N  G  N  A  I  Q  L  W  P  C  K  S  N  T  D  A  N  Q  L  W  T  L
AACGGAAACGCAATACAGTTGTGGCCATGCAAGTCTAATACAGATGCAAATCAGCTCTGGACTTTG
1386
K  R  D  N  T  I  R  S  N  G  K  C  L  T  T  Y  G  Y  S  P  G  V
AAAAGAGACAATACTATTCGATCTAATGGAAAGTGTTTAACTACTTACGGGTACAGTCCGGGAGTC
1452
Y  V  M  I  Y  D  C  N  T  A  A  T  D  A  T  R  W  Q  I  W  D  N
TATGTGATGATCTATGATTGCAATACTGCTGCAACTGATGCCACCCGCTGGCAAATATGGGATAAT
1518
G  T  I  I  N  P  R  S  S  L  V  L  A  A  T  S  G  N  S  G  T  T
GGAACCATCATAAATCCCAGATCTAGTCTAGTTTTAGCAGCGACATCAGGGAACAGTGGTACCACA
1584
L  T  V  Q  T  N  I  Y  A  V  S  Q  G  W  L  P  T  N  N  T  Q  P
CTTACAGTGCAAACCAACATTTATGCCGTTAGTCAAGGTTGGCTTCCTACTAATAATACACAACCT
1650
F  V  T  T  I  V  G  L  Y  G  L  C  L  Q  A  N  S  G  Q  V  W  I
TTTGTGACAACCATTGTTGGGCTATATGGTCTGTGCTTGCAAGCAAATAGTGGACAAGTATGGATA
1716
E  D  C  S  S  E  K  A  E  Q  Q  W  A  L  Y  A  D  G  S  I  R  P
GAGGACTGTAGCAGTGAAAAGGCTGAACAACAGTGGGCTCTTTATGCAGATGGTTCAATACGTCCT
1782
Q  Q  N  R  D  N  C  L  T  S  D  S  N  I  R  E  T  V  V  K  I  L
CAGCAAAACCGAGATAATTGCCTTACAAGTGATTCTAATATACGGGAAACAGTTGTCAAGATCCTC
1848
S  C  G  P  A  S  S  G  Q  R  W  M  F  K  N  D  G  T  I  L  N  L
TCTTGTGGCCCTGCATCCTCTGGCCAACGATGGATGTTCAAGAATGATGGAACCATTTTAAATTTG
1914
Y  S  G  L  V  L  D  V  R  A  S  D  P  S  L  K  Q  I  I  L  Y  P
TATAGTGGGTTGGTGTTAGATGTGAGGGCATCGGATCCGAGCCTTAAACAAATCATTCTTTACCCT
1980
L  H  G  D  P  N  Q  I  W  L  P  L  F  •  •
CTCCATGGTGACCCAAACCAAATATGGTTACCATTATTTTGATAGACAGATTACTCTCTTGCAGTG
2046                                  B-chain|
TGTATGTCCTGCCATGAAAATAGATGGCTTAAATAAAAAGGACATTGTAAATTTTGTAACTGAAAG
2112
GACAGCAAGTTATTGCAGTCCAGTATCTAATAAGAGCACAACTATTGTCTTGTGCATTCTAAATTT
2178
ATGGATGAATGTATGAATAAAGCTAATTATTTTGGTCATCAGACTTGATATCTTTTTGAATAAAAT
2244
AAATAATAATGTTTTTTCAAACTTATAAAACTAATGAATGATATGAATATAAATGCGGAGACTAGT
2310
CAATCTTTTATGTAATTCTATGATGATAAAAGCTT
```

FIG. 13A

```
                    15                  30                  45                  60                  75
CTT CAT CGT CGT CCA ACT GAC CTT GAG TGT TAG TTT CGC GGT AAG TTT GGG TAT AAG TGC CAC CAC CAG TGC CGG
                    90                  105                 120                 135                 150
CAG TGT AGT CAG TAG TTT GTT GCT GGA AGT CGT TAC CGC CAA ACT GCG TGT TAC CGC CTA GAT TAG ACT GTG GCT
                    165                 180                 195                 210                 225
GCT GGC GTT GAG GGA AAC CTG CCT GTA CGT GAG GCC CTA AAA AGC CAG AGA CCT CAC TCC CGG GGA GCC AGC ATG
                                                                                                Met
                    240                 255                 270                 285                 300
TCC ACT GCG GTC CTG GAA AAC CCA GGC TTG GGC AGG AAA CTC TCT GAC TTT GGA CAG GAA ACA AGC TAT ATT GAA
Ser Thr Ala Val Leu Glu Asn Pro Gly Leu Gly Arg Lys Leu Ser Asp Phe Gly Gln Glu Thr Ser Tyr Ile Glu
                    315                 330                 345                 360                 375
GAC AAC TGC AAT CAA AAT GGT GCC ATA TCA CTG ATC TTC TCA CTC AAA GAA GAA GTT GGT GCA TTG GCC AAA GTA
Asp Asn Cys Asn Gln Asn Gly Ala Ile Ser Leu Ile Phe Ser Leu Lys Glu Glu Val Gly Ala Leu Ala Lys Val
                    390                 405                 420                 435                 450
TTG CGC TTA TTT GAG GAG AAT GAT GTA AAC CTG ACC CAC ATT GAA TCT AGA CCT TCT CGT TTA AAG AAA GAT GAG
Leu Arg Leu Phe Glu Glu Asn Asp Val Asn Leu Thr His Ile Glu Ser Arg Pro Ser Arg Leu Lys Lys Asp Glu
                    465                 480                 495                 510                 525
TAT GAA TTT TTC ACC CAT TTG GAT AAA CGT AGC CTG CCT GCT CTG ACA AAC ATC ATC AAG ATC TTG AGG CAT GAC
Tyr Glu Phe Phe Thr His Leu Asp Lys Arg Ser Leu Pro Ala Leu Thr Asn Ile Ile Lys Ile Leu Arg His Asp
                    540                 555                 570                 585                 600
ATT GGT GCC ACT GTC CAT GAG CTT TCA CGA GAT AAG AAG AAA GAC ACA GTG CCC TGG TTC CCA AGA ACC ATT CAA
Ile Gly Ala Thr Val His Glu Leu Ser Arg Asp Lys Lys Lys Asp Thr Val Pro Trp Phe Pro Arg Thr Ile Gln
                    615                 630                 645                 660                 675
GAG CTG GAC AGA TTT GCC AAT CAG ATT CTC AGC TAT GGA GCG GAA CTG GAT GCT GAC CAC CCT GGT TTT AAA GAT
Glu Leu Asp Arg Phe Ala Asn Gln Ile Leu Ser Tyr Gly Ala Glu Leu Asp Ala Asp His Pro Gly Phe Lys Asp
                    690                 705                 720                 735                 750
CCT GTG TAC CGT GCA AGA CGG AAG CAG TTT GCT GAC ATT GCC TAC AAC TAC CGC CAT GGG CAG CCC ATC CCT CGA
Pro Val Tyr Arg Ala Arg Arg Lys Gln Phe Ala Asp Ile Ala Tyr Asn Tyr Arg His Gly Gln Pro Ile Pro Arg
                    765                 780                 795                 810                 825
GTG GAA TAC ATG GAG GAA GAA AAG AAA ACA TGG GGC ACA GTG TTC AAG ACT CTG AAG TCC TTG TAT AAA ACC CAT
Val Glu Tyr Met Glu Glu Glu Lys Lys Thr Trp Gly Thr Val Phe Lys Thr Leu Lys Ser Leu Tyr Lys Thr His
                    840                 855                 870                 885                 900
GCT TGC TAT GAG TAC AAT CAC ATT TTT CCA CTT CTT GAA AAG TAC TGT GGC TTC CAT GAA GAT AAC ATT CCC CAG
Ala Cys Tyr Glu Tyr Asn His Ile Phe Pro Leu Leu Glu Lys Tyr Cys Gly Phe His Glu Asp Asn Ile Pro Gln
```

*FIG. 13B*

```
                915                 930                 945                 960                 975
CTG GAA GAC GTT TCT CAA TTC CTG CAG ACT TGC ACT GGT TTC CGC CTC CGA CCT GTG GCT GGC CTG CTT TCC TCT
Leu Glu Asp Val Ser Gln Phe Leu Gln Thr Cys Thr Gly Phe Arg Leu Arg Pro Val Ala Gly Leu Leu Ser Ser
                990                 1005                1020                1035                1050
CGG GAT TTC TTG GGT GGC CTG GCC TTC CGA GTC TTC CAC TGC ACA CAG TAC ATC AGA CAT GGA TCC AAG CCC ATG
Arg Asp Phe Leu Gly Gly Leu Ala Phe Arg Val Phe His Cys Thr Gln Tyr Ile Arg His Gly Ser Lys Pro Met
                1065                1080                1095                1110                1125
TAT ACC CCC GAA CCT GAC ATC TGC CAT GAG CTG TTG GGA CAT GTG CCC TTG TTT TCA GAT CGC AGC TTT GCC CAG
Tyr Thr Pro Glu Pro Asp Ile Cys His Glu Leu Leu Gly His Val Pro Leu Phe Ser Asp Arg Ser Phe Ala Gln
                1140                1155                1170                1185                1200
TTT TCC CAG GAA ATT GGC CTT GCC TCT CTG GGT GCA CCT GAT GAA TAC ATT GAA AAG CTC GCC ACA ATT TAC TGG
Phe Ser Gln Glu Ile Gly Leu Ala Ser Leu Gly Ala Pro Asp Glu Tyr Ile Glu Lys Leu Ala Thr Ile Tyr Trp
                1215                1230                1245                1260                1275
TTT ACT GTG GAG TTT GGG CTC TGC AAA CAA GGA GAC TCC ATA AAG GCA TAT GGT GCT GGG CTC CTG TCA TCC TTT
Phe Thr Val Glu Phe Gly Leu Cys Lys Gln Gly Asp Ser Ile Lys Ala Tyr Gly Ala Gly Leu Leu Ser Ser Phe
                1290                1305                1320                1335                1350
GGT GAA TTA CAG TAC TGC TTA TCA GAG AAG CCA AAG CTT CTC CCC CTG GAG CTG GAG AAG ACA GCC ATC CAA AAT
Gly Glu Leu Gln Tyr Cys Leu Ser Glu Lys Pro Lys Leu Leu Pro Leu Glu Leu Glu Lys Thr Ala Ile Gln Asn
                1365                1380                1395                1410                1425
TAC ACT GTC ACG GAG TTC CAG CCC CTG TAT TAC GTG GCA GAG AGT TTT AAT GAT GCC AAG GAG AAA GTA AGG AAC
Tyr Thr Val Thr Glu Phe Gln Pro Leu Tyr Tyr Val Ala Glu Ser Phe Asn Asp Ala Lys Glu Lys Val Arg Asn
                1440                1455                1470                1485                1500
TTT GCT GCC ACA ATA CCT CGG CCC TTC TCA GTT CGC TAC GAC CCA TAC ACC CAA AGG ATT GAG GTC TTG GAC AAT
Phe Ala Ala Thr Ile Pro Arg Pro Phe Ser Val Arg Tyr Asp Pro Tyr Thr Gln Arg Ile Glu Val Leu Asp Asn
                1515                1530                1545                1560                1575
ACC CAG CAG CTT AAG ATT TTG GCT GAT TCC ATT AAC AGT GAA ATT GGA ATC CTT TGC AGT GCC CTC CAG AAA ATA
Thr Gln Gln Leu Lys Ile Leu Ala Asp Ser Ile Asn Ser Glu Ile Gly Ile Leu Cys Ser Ala Leu Gln Lys Ile
                1590                1605                1620                1635                1650
AAG TAA AGC CAT GGA CAG AAT GTG GTC TGT CAG CTG TGA ATC TGT TGA TGG AGA TCC AAC TAT TTC TTT CAT CAG
Lys ***
                1665                1680                1695                1710                1725
AAA AAG TCC GAA AAG CAA ACC TTA ATT TGA AAT AAC AGC CTT AAA TCC TTT ACA AGA TGG AGA AAC AAC AAA TAA
                1740                1755                1770                1785                1800
GTC AAA ATA ATC TGA AAT GAC AGG ATA TGA GTA CAT ACT CAA GAG CAT AAT GGT AAA TCT TTT GGG GTC ATC TTT
                1815                1830                1845                1860                1875
GAT TTA GAG ATG ATA ATC CCA TAC TCT CAA TTG AGT TAA ATC AGT AAT CTG TCG CAT TTC ATC AAG ATT AAT TAA
```

FIG. 13C

```
                    1890                     1905                     1920                     1935                     1950
AAT TTG GGA CCT GCT TCA TTC AAG CTT CAT ATA TGC TTT GCA GAG AAC TCA TAA AGG AGC ATA TAA GGC TAA ATG
                    1965                     1980                     1995                     2010                     2025
TAA AAC ACA AGA CTG TCA TTA GAA TTG AAT TAT TGG GCT TAA TAT AAA TCG TAA CCT ATG AAG TTT ATT TTC TAT
                    2040                     2055                     2070                     2085                     2100
TTT AGT TAA CTA TGA TTC CAA TTA CTA CTT TGT TAT TGT ACC TAA GTA AAT TTT CTT TAG GTC AGA AGC CCA TTA
                    2115                     2130                     2145                     2160                     2175
AAA TAG TTA CAA GCA TTG AAC TTC TTT AGT ATT ATA TTA ATA TAA AAA CAT TTT TGT ATG TTT TAT TGT AAT CAT
                    2190                     2205                     2220                     2235                     2250
AAA TAC TGC TGT ATA AGG TAA TAA AAC TCT GCA CCT AAT CCC CAT AAC TTC CAG TAT CAT TTT CCA ATT AAT TAT
                    2265                     2280                     2295                     2310                     2325
CAA GTC TGT TTT GGG AAA CAC TTT GAG GAC ATT TAT GAT GCA GCA GAT GTT GAC TAA AGG CTT GGT TGG TAG ATA
                    2340                     2355                     2370                     2385                     2400
TTC AGG AAA TGT TCA CTG AAT AAA TAA GTA AAT ACA TTA TTG AAA AGC AAA TCT GTA TAA ATG TGA AAT TTT TAT
                    2415                     2430                     2445
TTG TAT TAG TAA TAA AAC ATT AGT AGT TTA AAA AAA AAA AAA AAA AAA
```

HYBRID MOLECULES HAVING TRANSLOCATION REGION AND CELL-BINDING REGION

This is a continuation-in-part of patent application Ser. No. 08/102,387, filed Aug. 4, 1993, U.S. Pat No. 5,668,255, which is a continuation of application Ser. No. 07/722,484, filed Jun. 27, 1991, now abandoned, which is a CIP of application Ser. No. 07/538,276, filed Jun. 14, 1990, now abandoned, which is a CIP of application Ser. No. 07/456, 095, filed Dec. 22, 1989, now abandoned, which is a CIP of application Ser. No. 06/742,554, filed Jun. 7, 1985, now abandoned, which is a CIP of application Ser. No. 06/726, 808, filed Apr. 25, 1985, now abandoned, which is a continuation of application Ser. No. 06/618,199, filed Jun. 7, 1984, now abandoned.

BACKGROUND OF THE INVENTION

This invention relates to hybrid molecules having a cell-binding part and a translocation part.

The literature contains many examples of fused genes which code for hybrid proteins. For example, Villa-Komaroff et al., Proc. Natl. Acad. Sci. U.S.A. 75: 3727–3731, 1978, describes a fused gene made up of a eukaryotic structural gene fused to a non-cytoplasmic bacterial gene. The fused gene codes for a hybrid protein which is transported out of the cytoplasm.

Hybrid proteins also have been made by other methods (e.g., the coupling of two different protein molecules) which do not involve recombinant DNA techniques. For example, it has been proposed to form, by coupling, therapeutic hybrid proteins consisting of portions of toxin molecules coupled to a ligand capable of binding specifically to a selected class of cells. One attempt to make such a hybrid protein, reported in Chang et al., J. Biol. Chem. 252:1515–1522, 1977, resulted in a hybrid consisting of the diphtheria toxin A chain coupled to human placental lactogen hormone by cross-linking through a disulfide bond. The hybrid protein, although it bound to cells containing lactogen receptors, did not inhibit protein synthesis in those cells.

A hybrid protein consisting of the ricin toxin A chain coupled to the β chain of human chorionic gonadotropin hormone by similarly cross-linking through a disulfide bond has also been reported; although said to have specificity, its binding capacity has not been reported. Furthermore, extremely high concentrations were required to significantly inhibit protein synthesis in rat Leydig tumor cells, making it difficult to distinguish between "non-specific" entry caused by endocytosis and "specific" entry caused by transport of the toxic portion of the hybrid across the cytoplasmic membrane of the target cells (Oeltman et al., J. Biol. Chem. 254:1028–1032, 1979). The same shortcoming was found in a hybrid protein consisting of diphtheria A coupled to insulin using cystamine as the cross-linking agent (Miskimins et al., Biochem. Biophys. Res. Commun. 91:143–151, 1979). A hybrid consisting of ricin A coupled to epidermal growth factor (EGF) by means of a heterobifunctional cross-linker has also been made; the binding characteristics provided by the EGF are not limited to specific cells, but rather encompass a wide variety of cell types (Cawley et al., Cell 22:563–570, 1980).

As illustrated in FIG. 1, the natural diphtheria toxin molecule consists of several functional "domains" which can be characterized, starting at the amino terminal end of the molecule, as a hydrophobic leader signal sequence s (amino acids $Val_{-25}$-$Ala_{-1}$); enzymatically-active Fragment A (amino acids $Gly_1$-$Arg_{193}$); the proteolytically-sensitive disulfide loop $l_1$ (amino acids $Cys_{186}$-$Cys_{201}$), containing a cleavage domain; and Fragment B (amino acids $Ser_{194}$-$Ser_{535}$), which includes a translocation domain and a generalized binding domain flanking a second disulfide loop ($l_2$, amino acids $cys_{461}$-$Cys_{471}$).

The process by which diphtheria toxin intoxicates sensitive eukaryotic cells involves at least the following steps: (i) the binding domain of diphtheria toxin binds to specific receptors on the surface of a sensitive cell; (ii) while bound to its receptor, the toxin molecule is internalized into an endocytic vesicle; (iii) either prior to internalization, or within the endocytic vesicle, the toxin molecule undergoes a proteolytic cleavage in $l_1$ between fragments A and B; (iv) as the pH of the endocytic vesicle decreases to below 6, the toxin spontaneously inserts into the endosomal membrane; (v) once embedded in the membrane, the translocation domain of the toxin facilitates the delivery of Fragment A into the cytosol; (vi) the catalytic activity of Fragment A (i.e., the nicotinamide adenine dinucleotide-dependent adenosine diphosphate (ADP) ribosylation of the eukaryotic protein synthesis factor termed "Elongation Factor 2") causes the death of the intoxicated cell. It is apparent that a single molecule of Fragment A introduced into the cytosol is sufficient to shut down the cell's protein synthesis machinery and kill the cell. The mechanism of cell killing by Pseudomonas exotoxin A, and possibly by certain other naturally-occurring toxins, is very similar.

SUMMARY OF THE INVENTION

In general, the invention features, in one aspect, a hybrid molecule including a first part and a second part connected by a covalent bond, (a) the first part including a portion of the binding domain of a cell-binding ligand, which portion is able to cause the hybrid molecule of the invention to bind to an animal cell; and (b) the second part including a portion of a translocation domain of a protein, provided that (i) the hybrid molecule does not include an enzymatically-active portion of such protein, (ii) the first part and the second part are not segments of the same naturally-occurring polypeptide toxin, and (iii) the portion of the translocation domain, when covalently bonded to an enzymatically-active portion (i.e., the "effector region") of a toxin selected from diphtheria toxin, Pseudomonas exotoxin A, cholera toxin, ricin toxin, and Shiga-like toxin, is capable of translocating such effector region across the cytoplasmic membrane of the cell. "Translocation" here means the facilitation of movement of a chemical entity from the exterior surface of a cellular membrane (or what constituted the exterior surface prior to formation of an endocytic vesicle), through the membrane, and into the cytosol at the interior of the cell. A "translocation domain" is a segment of a protein which, when the protein is bound to the exterior surface of a cellular membrane, is capable of translocating some portion of that protein through the membrane.

In another aspect, the invention features a hybrid molecule including a first part, a second part, and a third part connected by covalent bonds, (a) such first part including a portion of the binding domain of a cell-binding ligand, which portion is effective to cause the hybrid molecule to bind to a cell of an animal;

(b) such second part including a portion of a translocation domain of a protein capable of translocating such third part across the cytoplasmic membrane of the cell; and (c) such third part including a chemical entity to be introduced into the cell, provided that (i) the second part and the third part are not segments of the same naturally-occurring polypeptide toxin; (ii) the second part is connected to the third part by at least one covalent bond (such as a disulfide bond, a peptide bond that is specifically susceptible to endocytic proteases, or a thioether bond) which is substantially cleaved under the chemical and enzymatic conditions that are likely to exist within endocytic vesicles of the targeted cell (such bond being herein specifically termed a "cleavable bond"); and either (iii) the hybrid molecule is a polypeptide produced by expression of a recombinant DNA molecule, or (iv) the first part and the second part are not segments of the same naturally-occurring polypeptide toxin, or both (iii) and (iv).

In preferred embodiments, the second part comprises at least a portion of the translocation domain of a naturally-occurring toxin (e.g. diphtheria toxin or Pseudomonas exotoxin A), and the ligand comprises a hormone (e.g. a polypeptide hormone such as insulin, Interleukin II (also termed "IL2"), Interleukin IV, Interleukin VI or EGF, or, alternatively, a steroid hormone); an antigen-binding, single-chain analog of a monoclonal antibody; or a polypeptide toxin capable of binding to the desired class of cells (more preferably, both the first and the second parts are derived from diphtheria toxin); where both the first and second parts are polypeptides, the hybrid molecule is preferably a recombinant protein; the hybrid molecule preferably additionally comprises a third part which is connected to the second part by at least one covalent bond and which is a chemical entity to be introduced into the cell (provided that where the third part is a polypeptide, the cleavable bond is a disulfide bond). More preferably, all three parts are polypeptides and the hybrid molecule is a recombinant protein (that is, a protein produced by recombinant DNA techniques); the third part and the second part are linked through a proteolytically-sensitive disulfide loop (defined below); the third part is an antigen-binding, single-chain analog of a monoclonal antibody (where such antigen is, for example, a viral protein such as the human immunodeficiency virus (HIV) protease), or alternatively, the enzymatically active portion of an enzyme (e.g., hexosaminidase A; α-1,4-glucosidase; phenylalanine hydroxylase; a protease; a nuclease; or a toxin such as cholera toxin, LT toxin, C3 toxin, Shiga toxin, *E.coli* Shiga-like toxin, ricin toxin, pertussis toxin, tetanus toxin, diphtheria toxin or Pseudomonas exotoxin A), and most preferably it supplies an enzymatic activity in which the cell is deficient, as, for example, in the case of a genetic deficiency. Where the enzyme is cholera toxin, the resulting hybrid molecule may be used to raise the cyclic AMP level within an animal cell: preferably, the cell so treated is a T-cell and the hybrid molecule includes at least a portion of the binding domain of IL2. By "proteolytically-sensitive disulfide loop" is meant a sequence of at least 5 amino acid residues (preferably from 6 to 30, and more preferably from 11 to 18) joined in series by peptide bonds, the first and last residues of which sequence are Cys residues which link to form a cystine disulfide bond. At least two of the remaining residues of the sequence together create a proteolytically-sensitive site: i.e., a peptide bond formed between two residues, the second (carboxyl side) of which may be, e.g., Arg, Lys, Phe, Tyr, or Trp. There is preferably also at least one Ser residue within the sequence of the loop. The loop, which may be a naturally-occurring feature of the second part or the third part, or may be engineered (e.g., from a synthetic DNA sequence) into the hybrid, joins the third part to the second part by two types of covalent linkages, peptide and sulfhydryl, ensuring that these two portions of the hybrid will remain associated with each other, even in the presence of extracellular proteases, until after the hybrid has bound to the target cell, but will separate at the appropriate stage. Both the proteolytically-sensitive peptide bond(s) within the disulfide loop and the disulfide bond itself are cleaved at some point prior to or during passage of the chemical entity through the cellular membrane of the endocytic vesicle, resulting in the release of the chemical entity into the cytosol, free of the receptor-bound cell-binding ligand portion (the first part), and translocation domain portion (the second part) of the hybrid.

The hybrid molecule of the invention includes the cholera toxin A/diphtheria toxin B'/IL2 hybrid polypeptide encoded by the plasmid illustrated in FIG. 6; the Shiga-like toxin A/diphtheria toxin B'/IL2 hybrid polypeptide encoded by the plasmid illustrated in FIG. 9; the ricin A/diphtheria toxin B'/IL2 hybrid polypeptide encoded by the plasmid illustrated in FIG. 12; the phenylalanine hydroxylase/diphtheria toxin fragment B hybrid polypeptide encoded by the plasmid illustrated in FIG. 14; an HIV protease-binding protein (HIVP-BP)/diphtheria toxin B'/IL2 hybrid polypeptide prepared as hereinafter described; and a Shiga-like toxin A/IL2 hybrid in which both the enzymatic activity and the translocation function are provided by the Shiga-like toxin A portion of the hybrid, and which contains a proteolytically-sensitive disulfide loop. Also included are biologically active mutational analogs of any of the above hybrid polypeptides. As used herein, a "biologically active mutational analog" is a polypeptide which exhibits the same type of cell-binding specificity and the same type of biological activity (e.g., a particular enzymatic or antigen-binding activity) as the listed hybrid polypeptide of which it is an analog, but which differs from such listed hybrid polypeptide by one or more deletions and/or one or more substitutions of one or more amino acid residues. Preferably, the amino acid sequence of the biologically active mutational analog shows at least a 70% (more preferably at least 80% and most preferably at least 90%) homology with the hybrid polypeptide of which it is an analog, and the analog exhibits at least 50% (more preferably, at least 75%) of a biological activity exhibited by the hybrid polypeptide of which it is an analog.

Also within the invention is a recombinant DNA molecule encoding any of the above hybrid polypeptide molecules (including biologically active mutational analogs), a vector including such a recombinant DNA molecule, a cell containing such a vector or recombinant DNA molecule (and which preferably is capable of expressing the recombinant DNA molecule to produce the hybrid polypeptide encoded by it), and a method of preparing the hybrid polypeptide molecule of the invention by permitting a cell containing a recombinant DNA molecule encoding the polypeptide (the "transformed cell") to express the recombinant DNA molecule.

In other preferred embodiments, the third part comprises a detectable label, more preferably a fluorescent moiety, a radioactive moiety, or an electron-dense moiety.

The invention also features a method of labeling a class of cells, which method involves contacting the cells with a hybrid molecule having a third part comprising a detectable label.

Also included in the invention are (1) a method of treating an animal having a deficiency in a certain enzyme, by administering to the animal an effective amount of a hybrid molecule comprising that enzyme; and (2) a method of treating a human patient infected with HIV, by administering to the patient an effective amount of a hybrid molecule having as its third part an HIV protease-binding, single-chain analog of a monoclonal antibody against HIV protease.

Based upon the observation that certain types of polypeptide toxins have three separate functional regions, one region which binds the molecule to particular receptors on the surface of a target cell, a second one which facilitates entry of the enzymatically-active region into the cytosol of the cell, and a third region which exhibits the enzymatic activity that characterizes the toxic effect of the molecule, the invention comprises bi- or tripartite hybrid molecules in which any of these regions may be replaced with functionally comparable regions from other sources. That is, the first functional region may be replaced with a particular binding moiety which binds the hybrid molecule to a selected class of cells, such as IL2 (which binds to high-affinity IL2 receptor-bearing T-cells), or α melanocyte stimulating hormone (αMSH, which binds to melanocytes), or a moiety which binds to a broad spectrum of cell types, as is characteristic of the binding domains of cholera toxin and diphtheria toxin; the second part may be taken from any type of polypeptide in which a translocation domain is identifiable, but will most likely be from a toxin molecule that translocates in a manner similar to diphtheria toxin and Pseudomonas exotoxin A. The optional third part may be any type of moiety that one wants to insert into the cell and that will fit through the channel in the membrane formed by the translocation domain: for example, a cell-killing enzyme such as Shiga toxin; a metabolic enzyme such as phenylalanine hydroxylase (the enzyme in which phenylketonurics are deficient); an antigen-binding, single-chain analog of a monoclonal antibody against an antigen that appears within the target cell; or a fluorescent label.

Although the medical community is rapidly expanding its understanding of the molecular bases of many diseases, one problem has particularly frustrated efforts to translate this understanding into rational protocols for treating the diseases: the problem of how to direct the appropriate therapy into the affected cells so that it can function properly to alleviate or cure the disease. By providing such a method, the present invention will have virtually unlimited applications: from treating genetic deficiency diseases by delivering to affected cells an enzyme supplying the missing function, to supplementing cellular levels of a particular enzyme or a scarce precursor or cofactor, to directing toxins or other poisons to destroy particular cells (such as adipocytes, cancer cells, or virus-infected cells), to counteracting viral infections such as HIV (which causes Acquired Immunodeficiency Syndrome ("AIDS")) by introducing into appropriate cells antibodies to viral proteins. The invention also provides a means for getting other, non-therapeutic substances, such as detectable labels, into targeted cells. The use of a translocation mechanism ensures that the hybrid will be effective in relatively low doses, since a high proportion of the substance of interest will be taken into the targeted cells.

To the extent that the two or three parts of the hybrids of the invention are polypeptides, they may be manufactured as a single hybrid recombinant protein, permitting reproducibility, consistency, and the precise control of composition which is desirable for any pharmaceutical product.

Other features and advantages of the invention will be apparent from the following description of the preferred embodiments thereof and from the claims.

DESCRIPTION OF THE PREFERRED EMBODIMENTS

The drawings will be briefly described.

Drawings

FIGS. 5-A and 5-B together are a representation of the nucleotide sequence of the *Vibrio cholerae* toxin gene, with amino acids shown below corresponding codons.

Figure 6:
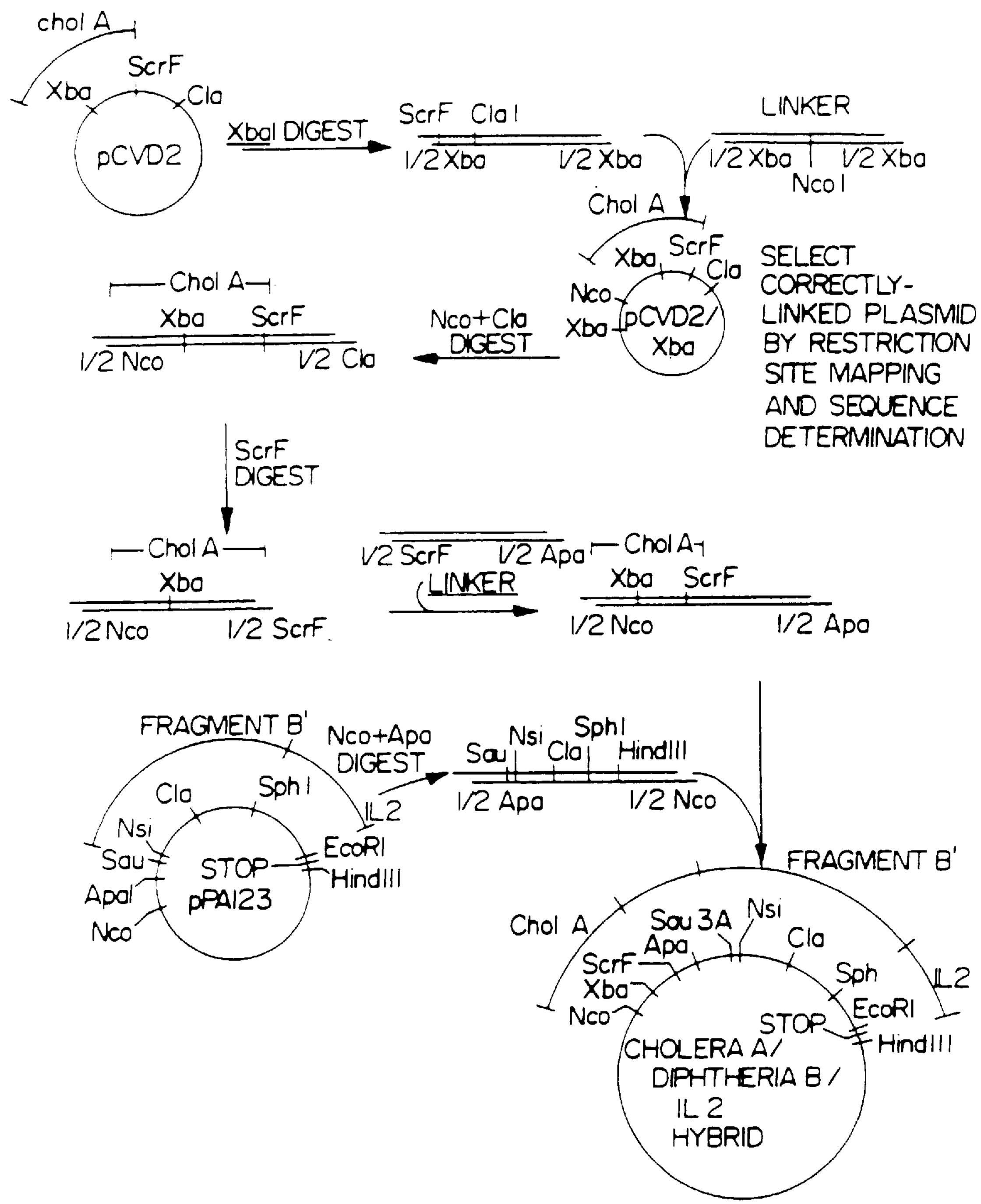

FIG. 6 is a diagrammatic representation of the cloning strategy followed to construct a plasmid encoding cholera toxin $A_1$-diphtheria toxin B'-IL2 hybrid.

Figure 7:
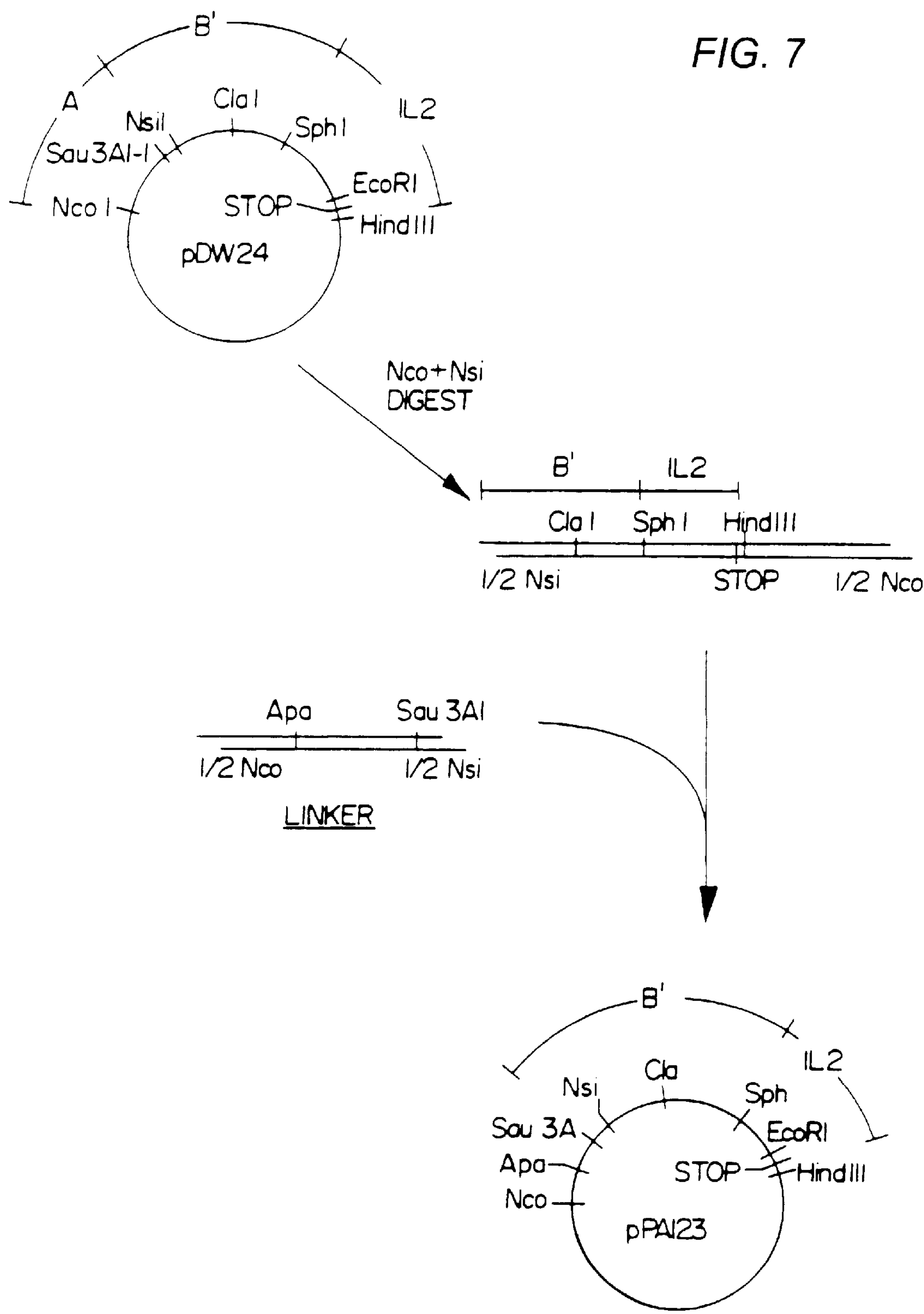

FIG. 7 is a diagrammatic representation of the cloning strategy followed in order to construct the plasmid pPA123.

FIGS. 8-A, 8-B and 8-C together are a representation of the nucleotide sequence of the *E.coli* bacteriophage H19B Shiga-like toxin gene, with amino acids shown below corresponding codons.

Figure 9:
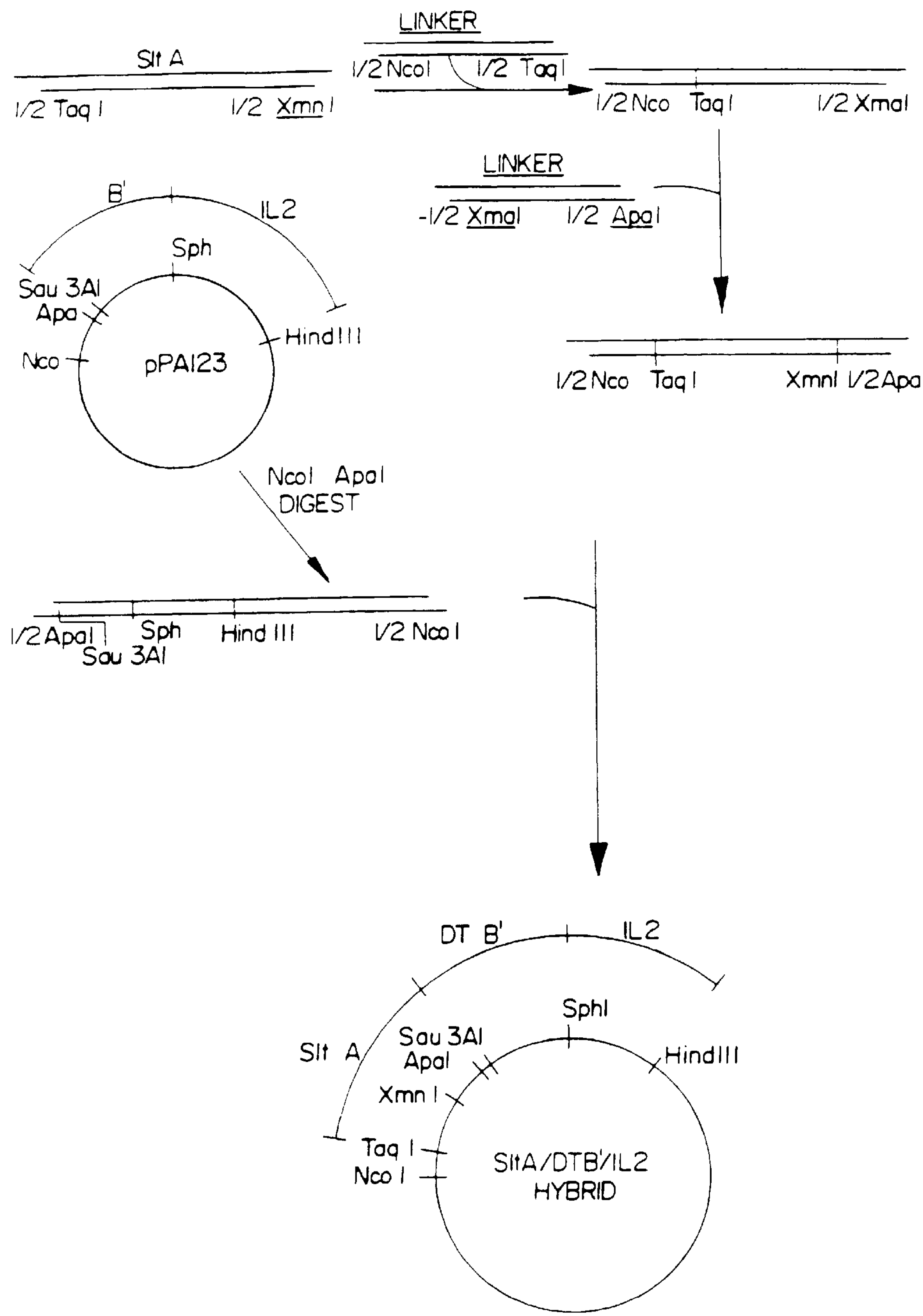

FIG. 9 is a diagrammatic representation of a cloning strategy proposed for constructing a plasmid encoding a Shiga-like toxin A-diphtheria toxin B'-IL2 hybrid.

Figure 10:
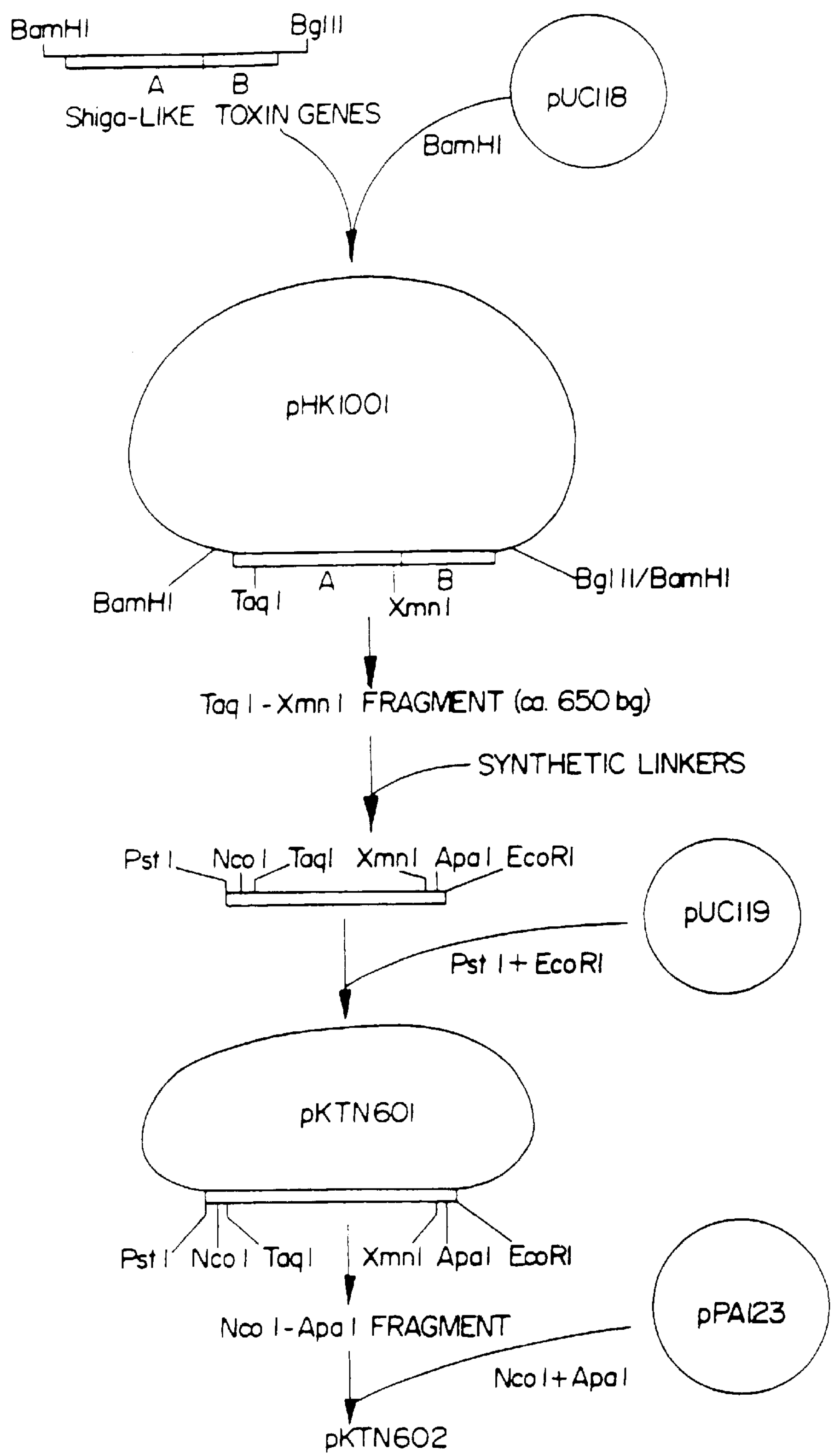

FIG. 10 is a diagrammatic representation of an alternative cloning strategy for constructing a plasmid encoding a Shiga-like toxin A-diphtheria toxin B'-IL2 hybrid.

Figure 1:
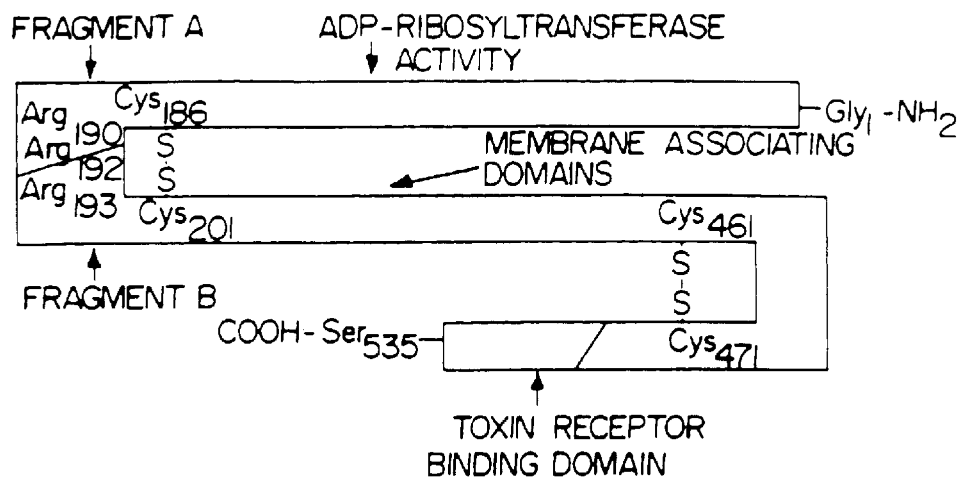
FIG. 1 is a diagrammatic representation of the diphtheria toxin molecule.
Figure 2:
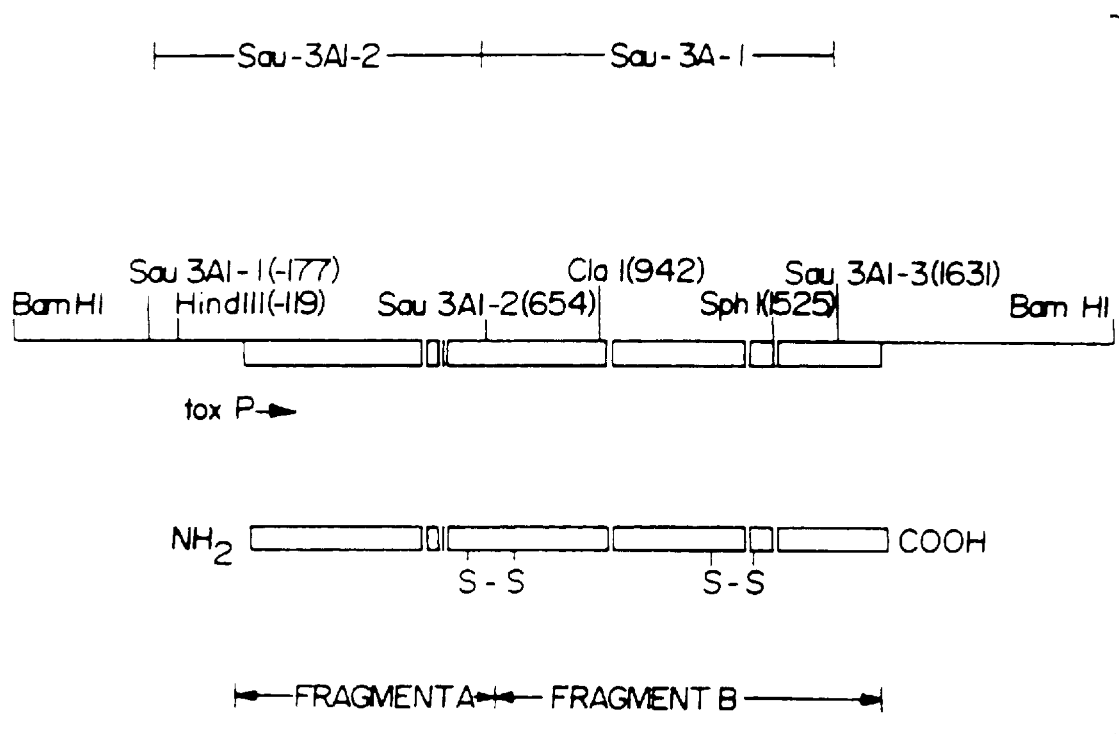
FIG. 2 is a restriction map showing the location and orientation of the diphtheria tox gene on the 3.9 kb BamHI restriction fragment of corynephage $\beta^{tox}$.

FIGS. 11-A and 11-B together are a representation of the nucleotide sequence of the *Ricinus communis* ricin gene, with amino acids shown above corresponding codons; this figure is adapted from FIG. 2 of Halling et al. (Nucl. Acids Res. 13:8019–8033, 1985).

Figure 12:
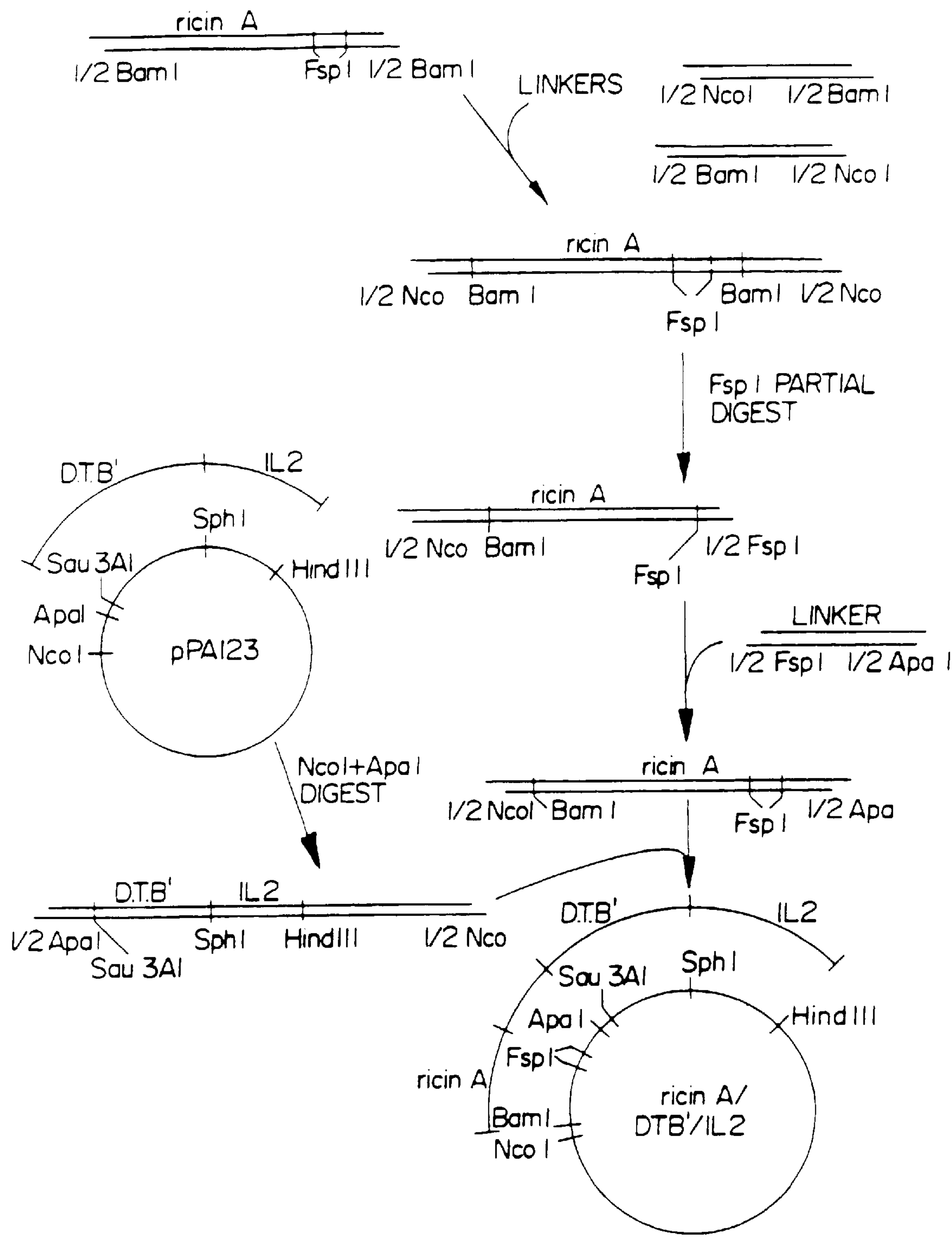

FIG. 12 is a diagrammatic representation of the cloning strategy proposed for constructing a plasmid encoding a ricin A-diphtheria toxin B'-IL2 hybrid.

FIGS. 13-A, 13-B and 13-C together are a representation of the nucleotide sequence of human phenylalanine hydroxylase cDNA, with amino acids shown below corresponding codons.

Figure 14:
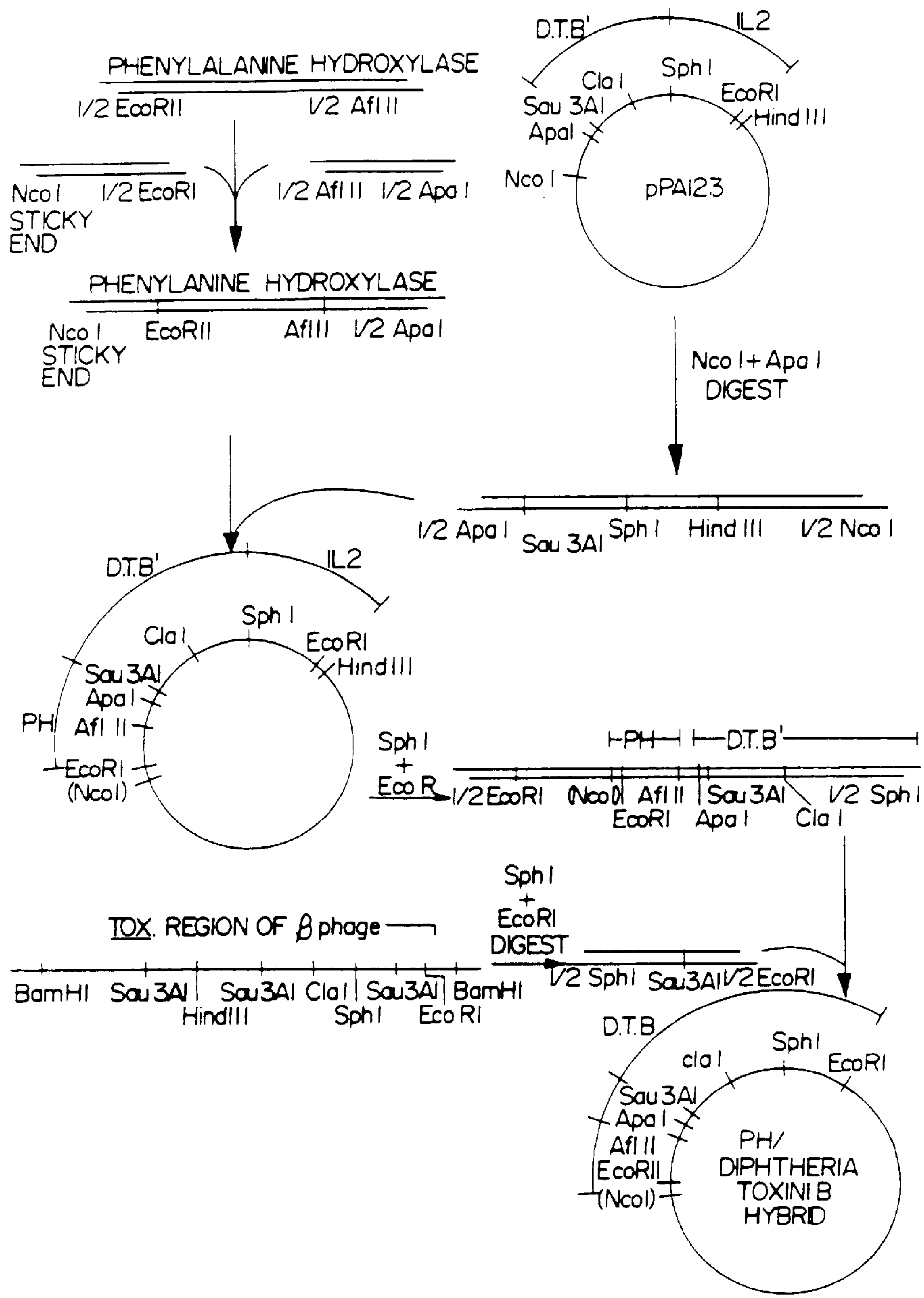

FIG. 14 is a diagrammatic representation of a cloning strategy proposed for constructing a plasmid encoding a phenylalanine hydroxylase-diphtheria toxin B hybrid.

STRUCTURE

One embodiment of the hybrid molecule of the invention is a two-part hybrid protein, comprising (1) a translocation domain, such as that of diphtheria toxin, and (2) a cell-binding domain from the same or a different origin as the translocation domain sequence. The cell-binding domain may be generalized (i.e. it is capable of binding the hybrid molecule to a wide variety of cell types) or specific for one or a few types of cells. The hybrid molecule may also contain a third part, linked to the translocation domain through a cleavable bond (as defined above) such that the translocation domain is capable of translocating the third part into or across the membrane of the cell to which the cell-binding portion of the hybrid is bound. This third part may be, for example, an enzymatically active polypeptide, an antigen-binding portion of a monoclonal antibody, or a detectable label such as a fluorescent dye. It may not, however, be a fragment of the same naturally-occurring molecule from which the translocation domain originates.

Naturally-occurring proteins which are known to have a translocation domain include diphtheria toxin and Pseudomonas exotoxin A, and may include other toxins and non-toxin molecules, as well. The translocation domains of diphtheria toxin and Pseudomonas exotoxin A are well characterized (see, e.g., Hoch et al., Proc. Natl. Acad. Sci. USA 82:1692–1696, 1985; Colombatti et al., J. Biol. Chem. 261:3030–3035, 1986; and Deleers et al., FEBS 160:82–86, 1983), and the existence and location of such a domain in other molecules may be determined by methods such as those employed by Hwang et al., Cell 48:129–136, 1987; and Gray et al., Proc. Natl. Acad. Sci. USA 81:2645–2649, 1984.

Figure 3:
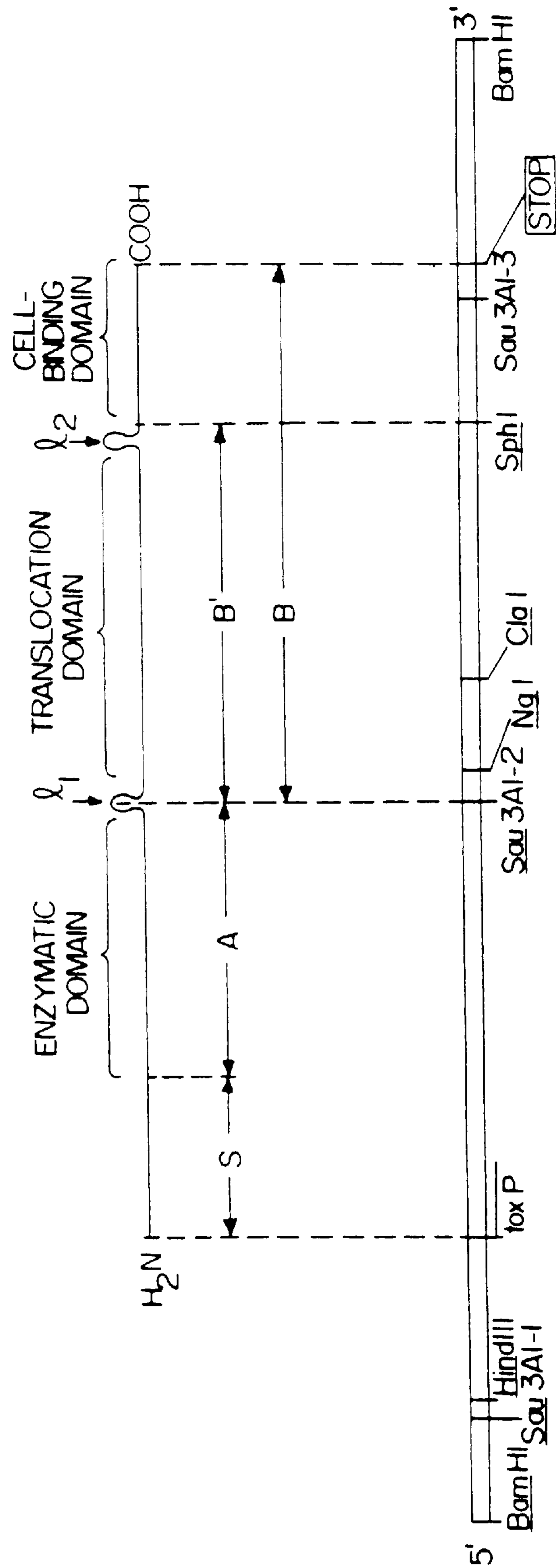
FIG. 3 is a representation of the diphtheria toxin gene and flanking regions, with the protein encoded shown above; the B' region is the region between the labeled Sau3A1-2 and SphI sites.
Figure 4:
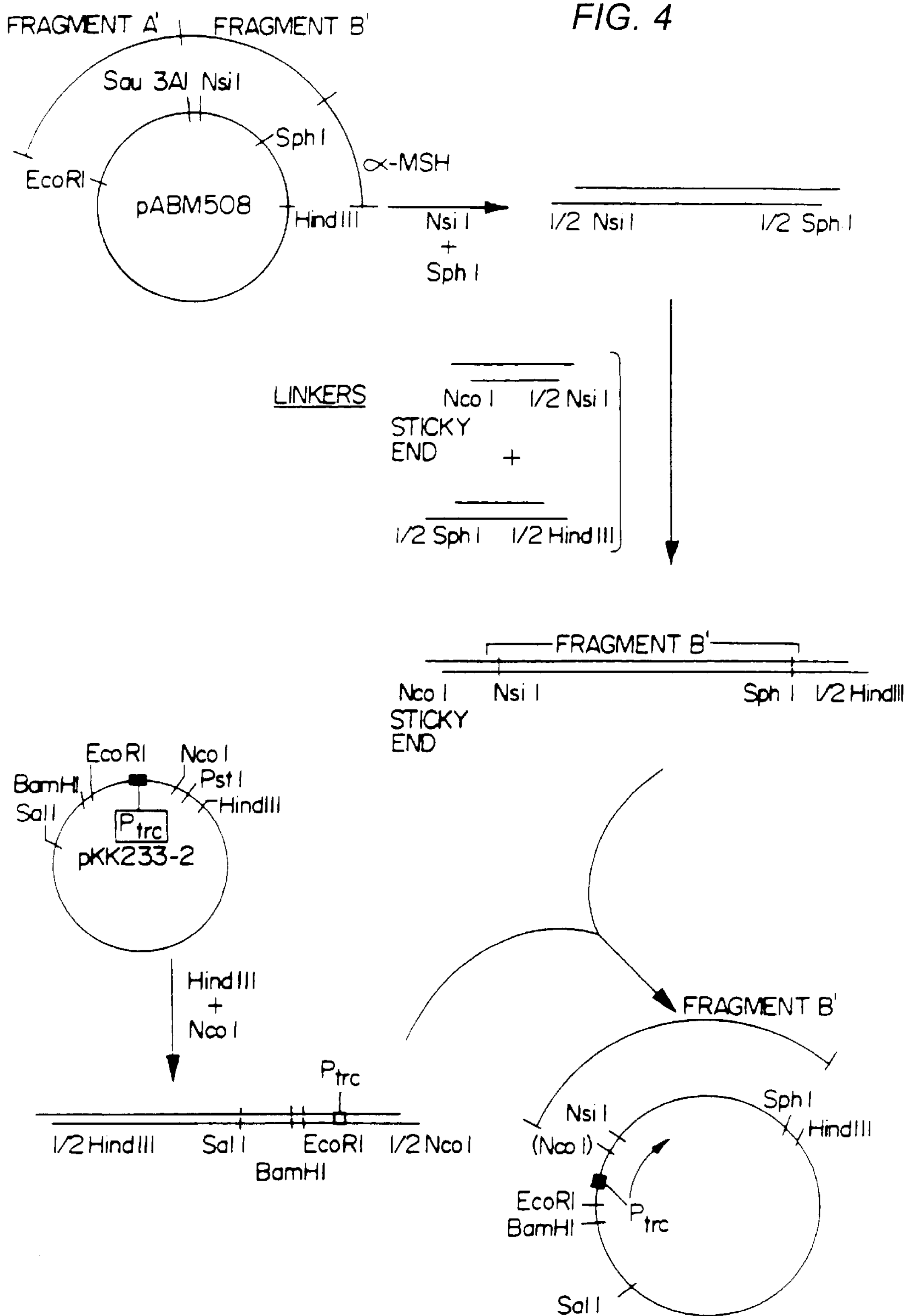
FIG. 4 is a diagrammatic representation of the strategy used to construct a plasmid encoding fragment B' of diphtheria toxin.

The segment of diphtheria toxin labelled "Fragment B" in FIG. 3 includes both the translocation domain and the generalized cell-binding domain of the naturally-occurring molecule. Truncation of Fragment B to the segment marked B' effectively eliminates the cell-binding function of diphtheria toxin while retaining the translocation function of the molecule. In the two-part hybrid of the invention, a portion of Fragment B encoded by a sequence ending at or downstream from the Sph1 restriction site may be used as long as it does not include sequences encoding a sufficient part of the diphtheria toxin receptor-binding domain to yield a functional receptor-binding domain.

The part of the hybrid protein contributed by the polypeptide ligand can consist of the entire ligand, or a portion of the ligand which includes the entire binding domain of the ligand, or an effective portion of the binding domain. When the ligand being used is large, it is desirable that as little of the non-binding portion as possible of the ligand be included, so that the binding domain of the molecule is positioned close to the translocation domain. It is also desirable to include all or most of the binding domain of the ligand molecule.

The polypeptide portions of the hybrids of the invention are conveniently made using recombinant DNA techniques involving forming the desired fused gene encoding the hybrid protein, and then expressing the fused gene. Chemical cross-linking is utilized only where one or more of the parts of the hybrid molecule are not polypeptides.

Standard procedures for DNA cloning, cell transformation and plasmid isolation (as described, for example, by Maniatis et al., Molecular Cloning: A Laboratory Manual. Cold Spring Harbor Laboratory, Cold Spring Harbor, N.Y., 1982), and for oligodeoxynucleotide synthesis, could be employed to carry out the following constructions.

EXAMPLE 1

Fusion of a Gene Fragment Encoding Diphtheria Toxin B' with Sequence Encoding Cell-binding Portions of Various Ligands; Labeling and Use of the Resultant Hybrid Polypeptides Referring to FIGS. 2 and 3, the location and orientation of the diphtheria tox operon on the 3.9 kb BamHI restriction fragment of corynephage $\beta^{tox+}$ allows the tox operon to be cleaved at a desired location, and the desired portion of the operon to be fused with the desired portion of the gene for a selected polypeptide ligand.

Gene fusions of the invention may be made as follows. First, the NsiI-SphI fragment encoding most of Fragment B' (FIG. 3) is isolated from the tox gene of plasmid pABM508 (Murphy et al., Proc. Natl. Acad. Sci. USA 83:8258–8262, 1986). The following linker is ligated into the 5' (NsiI) end:

```
5'      C ATG TCA GTA GGT AGC TCA TTG TCA TGC A 3'
3'             AGT CAT CCA TCG AGT AAC AGT       5'
encoding fmet-Ser-Val-Gly-Ser-Ser-Leu-Ser-Cys
          1/2                                1/2
          NcoI                               NsiI
```

and the following linker is ligated into the 3' (SphI) end:

```
5'       CAT GAA       3'
3' G TAC GTA CTT TCG A 5'
   1/2           1/2
   SphI          HindIII
```

The resulting fragment is then cloned into NcoI+HindIII-digested pKK233-2 (Pharmacia, Piscataway, N.J.).

This modification allows the expression of Fragment B' to be driven off the trc promoter ($P_{trc}$) in *E.coli*. The SphI site permits in-frame fusion with a gene sequence encoding the binding domain of a peptide ligand.

Generally, the manipulative operations are carried out using cloning vectors; e.g., phages or plasmids. The genetic material coding for the binding domain of the polypeptide ligand can be either DNA cloned from a natural source, or a synthetic oligonucleotide sequence. Generally the fused gene will reside on a cloning vector, e.g., a plasmid or a phage, which is used to transform cultured bacteria, yeast or tissue culture host cells. The hybrid protein is then harvested from the cells using conventional techniques. Purification of the hybrid proteins of the invention, regardless of the polypeptide ligand used, can be carried out via affinity chromatography, using a monoclonal antibody against diphtheria toxin Fragment B'.

The purified hybrid protein of the invention may be used as a transport system to carry a detectable label into specific cells. The label which is attached to the hybrid protein molecule can be any conventional atom or molecule used for diagnostic labeling; examples are radioactive labels such as $^{125}$I-compounds, technetium isotopes, NMR reporter groups, and fluorescent dyes. The most preferred labels are hydrophobic labels such as fluorescent dyes (most conventional fluorescent dyes happen to be hydrophobic) which are incorporated into the cytoplasmic membrane of target cells, as will be explained in more detail below. Labels can be attached to the hybrid protein according to conventional labeling techniques. Labels are used in an amount (e.g., one or two label molecules per protein molecule) which does not interfere with the binding or cell penetration functions of the hybrid protein molecule.

The labeled hybrid proteins of the invention can be used diagnostically to label a desired class of target cells, a class determined by the specific polypeptide ligand which imparts the binding domain of the hybrid molecule. The specific binding domain of the polypeptide ligand portion selectively binds to those cells; the labeled molecule is then taken up by the cells via receptor-mediated endocytosis, and the label subsequently is delivered to the cell membrane and/or the cytoplasm of the target cells.

The process by which a labeled hybrid protein of the invention can be incorporated into cells can be summarized as follows. The labeled hybrid protein is taken up by target cells via receptor-mediated endocytosis into an endocytic vesicle; thereafter a pH differential across the membrane of the endocytic vesicle is established as a result of the cell's ATP-dependent proton pump. The pH differential across the membrane causes the hybrid protein, including its lipid-associating portion and its label, to be inserted into the plane of the membrane of the endocytic vesicle. The hydrophobic nature of the hybrid protein causes it to remain in the membrane, protected from the rapid enzymatic degradation which would occur were the labeled protein to reside in the cytoplasm or in the lumen of the endocytic vesicle.

After insertion into the plane of the membrane of the endocytic vesicle, the labeled hybrid protein can "traffic", as follows. The-endocytic vesicle buds off from the cytoplasmic membrane and enters the cytoplasm of the cell, where it can merge with a lysosome into which the labeled hybrid protein is then incorporated. Alternatively, the endocytic vesicle can recycle to the cytoplasmic membrane of the cell. In either case, the label remains trapped in the target cell.

As is mentioned above, a major diagnostic use of the labeled hybrid proteins will be the in vivo and in vitro detection of metastatic loci, using conventional cell staining and labeling techniques. Such detection could be of particular value in surgery, by providing the surgeon with information needed to know how much tissue to excise when removing, e.g., metastatic melanoma cells.

EXAMPLE 2

Construction of a Cholera Toxin $A_2$-diphtheria Toxin B'-IL2 Gene, and Use of the Resultant Hybrid Protein Plasmid pCVD2 containing the coding sequence for the enzymatically-active $A_1$ fragment of cholera toxin (see FIG. 5) was prepared from a *Vibrio cholera* DNA library as described by Mekalanos et al. (Nature 306:551–557, 1983). FIG. 6 outlines the strategy employed in engineering a cholera toxin $A_1$-diphtheria toxin B'-IL2 gene. Briefly, pCVD2 was cleaved with the restriction enzyme XbaI at the unique XbaI site. The following synthetic linker, which has ½ of an XbaI site at each end, was ligated to the linearized plasmid in order to introduce a NcoI site upstream from the XbaI site:

```
    5' C TAG ACC ATG GGA AAT GAT GAT AAG TTA-
    3'       TGG TAC CCT TTA CTA CTA TTC AAT-
peptide:         fmet-Gly-Asn-Asp-Asp-Lys-Leu-
         1/2
         XbaI
(cont.)     - TAT CGG GCA GAT T      - 3'
```

-continued

```
            - ATA GCC CGT CTA AGA TC - 5'
            - Tyr-Arg-Ala-Asp-Ser-Arg
                               1/2
                               XbaI
```

The appropriate construct was selected by restriction site mapping and sequence determinations, and then was digested with Nco1 and ClaI to produce a Nco1-ClaI fragment. This in turn was digested with ScrFI. The 3' end of the resulting Nco1-ScrFI fragment was ligated to the following synthetic linker:

```
          5' - G GGT TCA GGG CC - 3'
          3' -   CCA AGT C      - 5'
peptide: Pro-Gly-Ser-Gly-Pro
             1/2            1/2
             ScrFI          ApaI
```

The polypeptide encoded by the resulting NcoI-ApaI fragment lacks the natural cholera toxin signal sequence, having instead fmet-Gly followed by the mature $A_1$ region of cholera toxin, followed by Gly-Ser-Gly-Pro. This construct can be cloned into a plasmid that encodes diphtheria toxin fragment B' fused to the human interleukin-2 gene (plasmid pPA123, FIG. 7). Plasmid pPA123 was constructed from plasmid pDW24 (Diane Williams, Ph.D. dissertation, Boston University School of Medicine, Department of Microbiology, Boston, Mass., 02118, 1989) as outlined in FIG. 7. Plasmid pDW24 encodes a diphtheria toxin fragment A-fragment B'-IL2 fusion protein that is expressed off the trc promoter in *E.coli*. The sequences encoding fragment A were deleted by digestion with the restriction endonucleases NcoI and NsiI. The following oligonucleotides were used to rebuild the fragment A/B disulfide loop ($l_1$) sequence, introduce an ApaI site on the 5' end of the loop, and recreate the NcoI site encoding the translation-initiating ATG codon:

```
5' -     C ATG GGG TCA GAT GGG CCC TGT GCA GGA AAT CGT GTC-
3' -           CC AGT CTA CCC GGG ACA CGT CCT TTA GCA CAG-
peptide:  fmet-Gly-Ser-Val-Gly-Pro-Cys-Ala-Gly-Asn-Arg-Val-
          1/2              ApaI
          NcoI
(cont.)     -AGG CGA TCA GTA GGT AGC TCA TTG TCA TGC A - 3'
```

-continued

```
-TCC GCT AGT CAT CCA TCG AGT AAC AGT-       - 5'

-Arg-Arg-Ser-Val-Gly-Ser-Ser-Leu-Ser-Cys

     Sau3AI                           1/2

                                      NsiI
```

Plasmid pPA123 resulted from ligating the above oligonucleotide fragment onto the NcoI-NsiI-digested pDW124 vector fragment. Plasmid pPA123 can now be used to fuse sequences encoding cholera toxin fragment $A_1$ to diphtheria toxin B'-IL2 as shown in FIG. 6. Plasmid pPA123 is digested with restriction enzymes NcoI and ApaI, and the resulting vector fragment is ligated to the modified cholera toxin fragment $A_1$ described above, to yield a plasmid encoding a cholera toxin $A_1$-diphtheria toxin B'-IL2 hybrid ("CTA/DTB'/IL2 hybrid"), which is expressed from the trc promoter on the plasmid.

Following expression of the recombinant gene in *E.coli*, the CTA/DTB'/IL2 hybrid protein can be isolated and used in appropriate treatment regimens: for example, as an adjunct to treatment with diphtheria toxin-IL2 hybrid. Diphtheria toxin-IL2 hybrid effectively targets the cell-killing ability of diphtheria toxin to cells bearing the IL2 receptor, such as certain leukemic T-cells. However, the pharmacological effectiveness of diphtheria toxin-IL2 hybrid is diluted by circulating endogenous IL2, which is naturally synthesized by activated T-cells and which competes with diphtheria toxin-IL2 hybrid for IL2 receptors on T-cells. By first exposing the target cells to CTA/DTB'/IL2 hybrid, the biological activity of cholera toxin can be harnessed to alleviate this problem. The $A_1$ subunit of natural cholera toxin enzymatically catalyzes the ADP-ribosylation of a GTP-binding regulatory component of the adenylate cyclase complex, resulting in the accumulation of cyclic AMP within the affected cell and thereby disrupting a multitude of cellular functions without killing the cell. Targeting the cholera toxin $A_1$ activity specifically to cells bearing the IL2 receptor will result in the temporary inhibition of IL2 synthesis within those cells. This permits depletion of the amount of circulating IL2 available to compete with diphtheria toxin-IL2 for IL2 receptors, without interfering with expression of IL2 receptors on the surfaces of the T-cells and without injuring non-targeted cells. Subsequent treatment with diphtheria toxin-IL2 will thus be more effective at killing T-cells than if CTA/DTB'/IL2 hybrid had not been used.

EXAMPLE 3

Construction of a Shiga-like Toxin A-diphtheria Toxin B'-IL2 Gene, and Use of the Resultant Hybrid Protein The DNA sequence and corresponding amino acid sequence for the A subunit of Shiga-like toxin ("SLT-A") are shown in FIG. 8. Bacteriophage H19B DNA from a strain of *E.coli* that produces SLT-A is prepared as described by Calderwood et al. (Proc. Natl. Acad. Sci. USA 84:4364–4368, 1987) and digested with TagI and XmnI. A TagI-XmnI fragment (approx. 650 bp) corresponding to most of the coding sequence for SLT-A (the "sltA gene") is isolated therefrom (see FIG. 9); the following oligonucleotide is then ligated onto the 5'(TagI) end of the fragment:

```
         5' - CATG GGA AAG GAA TTT ACC TTA GAC TTC T   - 3'

         3' -      CCT TTC CTT AAA TGG AAT CTG AAG AGC - 5'

peptide: fmet-Gly-Lys-Glu-Phe-Thr-Leu-Asp-Phe-Ser

              1/2                                1/2

              NcoI                               TagI
```

This oligonucleotide sequence provides an fmet-Gly coding sequence followed by a sequence coding for the first eight amino acids of the mature SLT A subunit, to replace the section of the natural gene (coding for the toxin signal peptide and same eight amino acids of the mature SLT A subunit) which was cleaved off during TagI digestion of the gene. Also provided by the oligonucleotide linker is a ½ NcoI site at the 5' end of the construct, to permit expression from the trc promoter of the hybrid plasmid.

The following oligonucleotide sequence, which regenerates the coding region (cleaved off by XmnI digestion) for the carboxyl end of the SLT A subunit up to the initial Cys codon, and introduces an ApaI restriction site, is ligated to the 3' (XmnI) end of the sltA gene fragment:

```
    5' - ATT TCT TTT GGA AGC ATT AAT GCA ATT CTG-

    3' - TAA AGA AAA CCT TCG TAA TTA CGT TAA GAC-

peptide: Ile-Ser-Phe-Gly-Ser-Ile-Asn-Ala-Ile-Leu-

         1/2

         XmnI

(cont.) -GGA AGC GTG GCA TTA ATA CTG AAT GGG CC -3'

        -CCT TCG CAC CGT AAT TAT GAC TTA C      -5'

        -Gly-Ser-Val-Ala-Leu-Ile-Leu-Asn-Gly-Pro

                                          1/2 ApaI
```

The NcoI-ApaI slta gene sequence can be ligated into a NcoI+ApaI-digested plasmid pPA123 (FIG. 7) to yield a SLTA-diphtheria toxin B'-IL2 ("SLTA/DTB'/IL2 hybrid") gene that can be expressed in *E.coli* from the trc promoter on the plasmid (see FIG. 9).

An alternative cloning strategy for constructing a plasmid encoding a Shiga-like toxin A- diphtheria toxin B'-IL2 hybrid is illustrated in FIG. 10.

Purified SLTA/DTB'/IL2 hybrid protein would be useful as a treatment for conditions involving overproduction of cells bearing IL2 receptors, such as certain T-cell lymphomas and organ transplant rejection crises. As is the case for diphtheria toxin-IL2, the IL2 portion of the hybrid causes the hybrid to attach specifically to IL2-receptor-bearing cells, and the diphtheria toxin B' portion acts to insert the enzymatic portion of the hybrid into the targeted cell; the enzymatic portions of both types of hybrid toxins then act on the protein synthesis machinery in the cell to shut down protein synthesis, thus killing the cell. The difference between these two types of hybrid toxins is the nature of their enzymatic activities: the enzymatic portion of diphtheria toxin-IL2 hybrid catalyzes the ADP-ribosylation by nicotinamide adenine dinucleotide of Elongation Factor 2, thereby inactivating this factor which is necessary for protein synthesis, while the enzymatic portion of SLTA/DTB'/IL2 hybrid is a ribonuclease capable of cleaving ribosomal RNA at a critical site, thereby inactivating the ribosome. SLTA/DTB'/IL2 hybrid would therefore be useful as a treatment for the same indications as diphtheria toxin-IL2 hybrid, and could be substituted if, for example, the proliferating T-cells develop a resistance to the latter hybrid toxin.

EXAMPLE 4

Construction of Ricin A-diphtheria Toxin B'-IL2 Gene, and Use of the Resultant Hybrid Protein A genomic clone bank of castor bean (*Ricinus communis*) DNA is prepared as described in Halling et al., Nucl. Acids Res. 13:8019–8033, 1985, and a ~780 bp BanI fragment of the ricin gene, corresponding to most of the ricin A domain (the enzymatic domain) and a portion of the ricin A-to-B linker peptide, is isolated therefrom (see FIG. 11). The following synthetic oligonucleotide is ligated onto both ends of the fragment, phosphorylating only the bottom strand of DNA shown:

```
5' -      C ATG GCT ATA TTC CCC AAA CAA TAC CCA ATT-
3' -             CGA TAT AAG GGG TTT GTT ATG GGT TAA-
Peptide:  fmet-Ala-Ile-Phe-Pro-Lys-Gln-Tyr-Pro-Ile-
         1/2
         NcoI
(cont.) -ATA AAC TTT ACC ACA GCG G       - 3'
        -TAT TTG AAA TGG TGT CGC CCA CG - 5'
        -Ile-Asn-Phe-Thr-Thr-Ala-Gly-Ala
                                  1/2
                                  BanI
```

The resulting ligated fragment (illustrated in FIG. 11) is partially digested with FspI, and the ~780 bp band corresponding to a BanI-FspI ricin A gene fragment with a NcoI-BanI linker at the 5' end is isolated (see FIG. 11). The NcoI-BanI linker supplies the mature ricin A N-terminal amino acid codons which were cleaved from the fragment during BanI digestion, as well as the codons for fmet-Ala to replace the natural ricin A signal peptide.

The following oligonucleotide is ligated onto the 3' (FspI) blunt end of the fragment, phosphorylating only the top strand shown:

```
          5' - GCA CCT CCA CCA TCG TCA CAG TTT GGG CC - 3'
          3' - CGT GGA GGT GGT AGC AGT GTC AAA C      - 5'
Peptide:       Ala-Pro-Pro-Pro-Ser-Ser-Gln-Phe-Gly-Pro
               1/2                                1/2
               FspI                               ApaI
```

This linker supplies the ricin A coding sequence cleaved from the 3' end of the ricin A fragment during the FspI digest, plus a ½ ApaI site for fusion to plasmid pPA123.

The completed construct is then cloned into NcoI/ApaI-digested pPA123 to yield a ricin A-diphtheria toxin B'-IL2 gene that can be expressed in *E.coli* from the trc promoter on the plasmid (see FIG. 12).

Purified ricin A-diphtheria toxin B'-IL2 hybrid, like the SLTA/DTB'/IL2 hybrid of Example 3, inactivates ribosomes in cells bearing IL2 receptors, resulting in cessation of protein synthesis and death of the targeted cells. The ricin A hybrid would thus have the same applications as SLTA/DTB'/IL2 hybrid, as discussed in Example 3.

EXAMPLE 5

Construction of Phenylalanine Hydroxylase-diphtheria Toxin B Gene, and Use of the Resultant Hybrid Protein.

A human liver cDNA library is screened for phenylalanine hydroxylase ("PH") cDNA as described by Kwok et al., Biochem. 24:556–561, 1985. The approximately 1160-bp EcoRII-AflII fragment that encodes most of the PH protein is isolated (see FIGS. 13 and 14). The following linkers are ligated onto the 5' EcoRII end in order to recreate the 5' coding sequences and incorporate an NcoI site:

```
5' - C ATG TCC ACT GCG GTC CTG GAA AAC          - 3'
3' -       AGG TGA CGC CAG GAC CTT TTG GGT CC  - 5'
     fmet-Ser-Thr-Ala-Val-Leu-Gln-Asn-Pro-Gly
     NcoI                                1/2
     sticky end                          EcoRII
```

The following linkers are ligated onto the 3' AflII end to complete the PH coding sequence and to include an ApaI restriction site in the correct translational reading frame for fusion to diphtheria toxin fragment B sequences (FIG. 14):

```
5' - TT AAG ATT TTG GCT GAT TCC ATT AAC AGT GAA ATT GGA-

3' -      C TAA AAC CGA CTA AGG TAA TTG TCA CTT TAA CCT-

        Lys-Ile-Leu-Ala-Asp-Ser-Ile-Asn-Ser-Glu-Ile-Gly-

     1/2

     AflII

(cont.) -ATC CTT TGC AGT GCC CTC CAG AAA ATA AAG GGG CC - 3'

        -TAG GAA ACG TCA CGG GAG GTC TTT TAT TTC C      - 5'

        -Ile-Leu-Cys-Ser-Ala-Leu-Gln-Lys-Ile-Lys-Gly-Pro

                                                     1/2

                                                     ApaI
```

This fragment is then ligated onto the NcoI-ApaI digested pPA123 vector (FIG. 14) resulting in a plasmid that encodes phenylalanine hydroxylase fused to diphtheria toxin B'-IL-2. Finally, this plasmid is digested with EcoRI and SphI to remove IL-2 encoding sequences, which are replaced by the approximately 230 bp SphI-EcoRI fragment of corynebacteriophage β that encodes the 3' end of diphtheria toxin fragment B (FIG. 14). This completed construct codes for a PH-diphtheria toxin B hybrid protein that can be expressed in *E.coli* from the trc promoter on the plasmid (see FIG. 14).

The inherited disorder phenylketonuria, in which the inability to metabolize phenylalanine leads to an accumulation of excess phenylalanine and possible brain damage in affected individuals, has been attributed to a genetic deficiency of the enzyme PH. By constructing a molecule in which active PH enzyme is linked to the cell-binding and translocation domains of diphtheria toxin Fragment B, the enzyme can be targeted to and incorporated into the broad range of cells which native diphtheria toxin normally attacks, achieving the widespread therapy that is called for by a defect such as phenylketonuria. This cloning strategy would be applicable to the construction of other hybrids useful in the treatment of other genetic defects.

EXAMPLE 6

Construction of an HIV Protease-binding Protein-diphtheria Toxin B'-IL2 Gene, and Use of the Resultant Hybrid Protein.

A recombinant gene expressing a novel protein, an antigen-binding, single-polypeptide-chain analog of a monoclonal antibody composed of an antibody variable light-chain amino acid sequence ($V_L$) linked to a variable heavy-chain sequence ($V_H$) by a linker peptide, is constructed by the method of Bird et al., Science 242:423–426, 1988, based upon the $V_L$ and $V_H$ sequences of a monoclonal antibody specific for and able to inactivate HIV protease (Hansen et al., Embo J. 7:1785–1791, 1988) and a linker peptide designed by the method of Bird et al. The ends of the $V_L$-linker-$V_H$ gene are modified with appropriate restriction enzymes and synthetic DNA linkers in order to produce an intact $V_L$-linker-$V_H$ gene having ½ of a NcoI site at the 5' end and ½ of an ApaI site at the 3' end. The gene is then cloned into NcoI+ApaI-digested pPA123 to produce a plasmid expressing, from the trc promoter, an HIV protease-binding protein-diphtheria toxin B'-IL2 hybrid protein ("HIVP-BP/DTB'/IL2 hybrid").

Following expression of the recombinant gene in *E.coli*, the HIVP-BP/DTB'/IL2 hybrid protein can be isolated and used to treat an HIV infection in a human patient. The HIV virus infects and proliferates within T-cells, commandeering the cellular protein synthesis machinery to produce multiple copies of its own proteins. One viral protein in particular, the HIV protease, plays a critical role in the processing of other viral proteins; identifying a way to inactivate this protease within the infected cell has been the focus of much recent effort toward developing an effective AIDS therapy (see, e.g., Hansen et al.). The HIVP-BP/DTB'/IL2 hybrid delivers a viral protease-specific inhibitor specifically to activated T-cells bearing the IL2 receptor, and thus can be effective at low dosages, with little or no toxicity to other types of cells. This technology could be applied as well to other viral infections or genetic disorders.

OTHER EMBODIMENTS

Other embodiments are within the following claims. For example, any cell-specific polypeptide ligand can be used which has a binding domain specific for the particular class of cells which are to be labeled. Polypeptide hormones are useful such ligands. Hybrid protein made using the binding domain of α or β MSH, for example, can selectively bind to melanocytes, rendering hybrids, once labelled with a detectable label, useful in the diagnosis of melanoma and the in vivo and in vitro detection of metastic melanoma loci. Such a hybrid, when attached to an enzymatically-active portion of a toxin molecule instead of to a detectable label, could be utilized to deliver that toxic activity specifically to the target melanoma cells. Other ligands provide different specificities: e.g., the binding domain of substance P recognizes receptors on the surfaces of neurons involved in the transmission of pain, so that labeled hybrids made using substance P can be used to map areas of the nervous system containing substance P receptors. Other specific-binding ligands which can be used include insulin, somatostatin, EGF, and Interleukins I, II, III, IV and VI. Interleukin II is of particular importance because of its role in allergic reactions and autoimmune diseases such as Systemic.Lupus Erythmatosis (SLE), involving activated T cells. Other useful polypeptide ligands having cell-specific binding domains are follicle stimulating hormone (specific for ovarian cells), luteinizing hormone (specific for ovarian cells), thyroid stimulating hormone (specific for thyroid cells), vasopressin (specific for uterine cells, as well as bladder and intestinal cells), prolactin (specific for breast cells), and growth hormone (specific for certain bone cells). Alternatively, a relatively indiscriminate cell-binding ligand (such as that of diphtheria toxin or ricin toxin) capable of binding to a wide variety of cell types in an organism can be used to effect widespread introduction of a specific chemical entity into cells of that organism, where more specific targeting is not the goal.

For a number of cell-specific ligands, the region within each such ligand in which the binding domain is located is now known. Furthermore, recent advances in solid phase polypeptide synthesis enable those skilled in this technology to determine the binding domain of practically any such ligand, by synthesizing various fragments of the ligand and testing them for the ability to bind to the class of cells to be labeled. Thus, the hybrid molecules of the invention need not include an entire ligand, but rather may include only a fragment of a ligand which exhibits the desired cell-binding capacity. Likewise, analogs of the ligand or its cell-binding region having minor sequence variations may be synthesized, tested for their ability to bind to cells, and incorporated into the hybrid molecules of the invention. Other potential ligands include monoclonal antibodies or antigen-binding, single-chain analogs of monoclonal antibodies, where the antigen is a receptor or other moiety expressed on the surface of the target cell membrane.

The translocation function of the hybrid molecule may be supplied by an appropriate piece of a polypeptide other than diphtheria toxin, but which is capable of translocating in a manner analogous to that of diphtheria toxin (e.g., Pseudomonas exotoxin A, botulinum neurotoxin, or ricin), or in any other manner which accomplishes the objective of translocating the functional "third part" of the hybrid molecule into the cell's cytoplasm.

The chemical entity to be inserted into the cell can vary widely and still be within the invention. For example, the enzyme which is genetically deficient in Tay-Sachs disease, hexosaminidase A, could be attached to a hybrid having a cell-binding domain specific for the cells most affected by the disease, nerve cells. Patients suffering from type 2 glycogenosis might be treated with a hybrid comprising α-1,4-glucosidase linked to the translocation segment of diphtheria toxin linked to insulin, which would largely target muscle cells, hepatocytes, and lymphocytes. (See Poznansky et al., Science 223:1304–1306, 1984.) These are simply examples: any other enzyme deficiency disease for which the natural enzyme or its gene has been sequenced (or is amenable to sequencing by one skilled in the art, without undue experimentation) could be treated with a hybrid comprising the active enzyme linked to a translocation domain linked to an appropriate cell-binding ligand. Further, the chemical entity alternatively can be a nucleic acid (e.g. DNA) encoding the polypeptide of interest.

Intracellular viral and bacterial infections could be treated by an appropriate hybrid: for example, a hybrid which delivers into the cell a potent antibiotic, or a recombinant $V_L$-linker-$V_H$ antigen-binding polypeptide which specifically binds viral particles or proteins.

Likewise, the hybrid of the invention will be useful for specifically destroying certain cells. Besides the cholera toxin $A_1$-hybrid, ricin A-hybrid and Shiga-like toxin A-hybrid exemplified above, a cell-killing function may be provided by the enzymatically-active portion of any polypeptide toxin, including but not limited to LT toxin, C3 toxin, Shiga toxin, pertussis toxin, tetanus toxin and Pseudomonas exotoxin A. Cells to be targeted might include cancer cells, virus-infected cells, or adipocytes.

The invention includes biologically active mutational analogs of hybrid polypeptides described above. By manipulating the recombinant DNA sequence encoding the subject hybrid polypeptide using methods well known to those of ordinary skill in the art of genetic engineering, a series of mutations involving deletions and/or substitutions of individual or multiple base pairs in such recombinant DNA sequence is first created. Each such mutated sequence is then inserted into an expression vector and expressed in an appropriate expression system. The biological activity of the mutational analog so produced can then be compared to that exhibited by the hybrid molecule of which it is an analog (the "parent polypeptide"). The particular assay used will depend upon the particular enzymatic activity and cell-binding specificity of the parent polypeptide. For example, mutational analogs of the Shiga-like toxin A/diphtheria toxin B'/IL2 (SLTA/DTB'/IL2) hybrid, the cholera toxin $A_1$/diphtheria toxin B'/IL2 (CTA/DTB'/IL2) hybrid, and the ricin A/diphtheria toxin B'/IL2 hybrid may be tested and compared to their respective parent polypeptides in the following cell cytotoxicity assay, which is specific for toxins capable of binding to IL2 receptor-bearing cells.

Assay

Cultured HUT 102/6TG (Tsudo et al., Proc. Natl. Acad. Sci. USA 83:9694, 1986) or YT2C2 (Teshigawari et al., J. Exp. Med. 165:223, 1987) cells are maintained in RPMI 1640 medium (Gibco, Grand Island, N.Y.) supplemented with 10% fetal bovine serum (Cellect, GIBCO), 2 mM glutamine, and penicillin and streptomycin to 50 IU and 50 μg/ml, respectively. Cells are seeded in 96-well V-bottomed plates (Linbro-Flow Laboratories, McLean, Va.) at a concentration of $5\times10^4$ per well in complete medium. Putative toxins are added to varying concentrations ($10^{-12}$M to $10^{-6}$M) and the cultures are incubated for 18 hrs. at 37° C. in a 5% $CO_2$ atmosphere. Following incubation, the plates are centrifuged for 5 min. at 170×g, and the medium removed and replaced with 200 μl leucine-free medium (MEM, Gibco) containing 1.0 μCi/ml [$^{14}$C]-leucine (New England Nuclear, Boston, Mass.). After an additional 90 min. at 37° C., the plates are centrifuged for 5 min. at 170×g, the medium is removed and the cells are lysed by the addition of 4 M KOH. Protein is precipitated by the addition of 10% trichloroacetic acid and the insoluble material is then collected on glass fiber filters using a cell harvester (Skatron, Sterling, Va.). Filters are washed, dried, and counted according to standard methods. Cells cultured with medium alone serve as the control.

Where IL4 replaces IL2 as the cell-binding portion of the resulting hybrid, the hybrid and its mutational analogs may be tested by a similar assay utilizing CT4R cells (William E. Paul, NIH), P815 cells (ATCC), or CTLL2 (ATCC), seeded at $1\times10^4$ cells per well and incubated for 40 hours.

What is claimed is:

1. A hybrid molecule comprising a first part, a second part, and a third part connected by covalent bonds, (a) wherein said first part comprises a portion of the binding domain of a cell-binding ligand effective to cause said hybrid molecule to bind to a cell of an animal;

(b) wherein said second part comprises a portion of a translocation domain of a naturally occurring protein which translocates said third part across the cytoplasmic membrane into the cytosol of the cell; and (c) wherein said third part comprises a chemical entity to be introduced into the cell, wherein each of said first part and said third part is non-native with respect to said naturally occurring protein, and further wherein said covalent bond connecting said second part and said third part is a cleavable bond, provided that when said second part comprises a portion of a translocation domain of Pseudomonas exotoxin, said third part is not a polypeptide.

2. The hybrid molecule of claim 1, wherein said cell-binding ligand is a polypeptide.

3. The hybrid molecule of claim 1, wherein said third part is a detectable label.

4. The hybrid molecule of claim 1, wherein said third part is a polypeptide.

5. The hybrid molecule of claim 1, wherein the covalent bond connecting said second and third parts is a disulfide bond.

6. The hybrid molecule of claim 1, wherein the covalent bond connecting said second and third parts is a thioether bond.

7. The hybrid molecule of claim 1, wherein said naturally occurring protein of (b) is botulinum neurotoxin.

8. The hybrid molecule of claim 1, wherein said naturally occurring protein of (b) is Shiga-like toxin.

9. The hybrid molecule of claim 2, wherein said first part comprises the binding domain of said cell-binding polypeptide ligand.

10. The hybrid molecule of claim 2, wherein said first part comprises the cell-binding polypeptide ligand.

11. The hybrid molecule of claim 2, wherein said cell-binding polypeptide ligand is a hormone.

12. The hybrid molecule of claim 2, wherein said cell-binding polypeptide ligand is an antigen-binding, single-chain analog of a monoclonal antibody.

13. The hybrid molecule of claim 2, wherein said first part comprises a monoclonal antibody.

14. The hybrid molecule of claim 2, wherein said first part comprises a portion of the binding domain of a polypeptide toxin.

15. The hybrid molecule of claim 3, wherein said detectable label is a fluorescent moiety, a radioactive moiety, or an electron-dense moiety.

16. The hybrid molecule of claim 4, wherein said polypeptide is an antigen-binding, single-chain analog of a monoclonal antibody.

17. The hybrid molecule of claim 4, wherein said polypeptide comprises the enzymatically active portion of an enzyme.

18. The hybrid molecule of claim 4, wherein said polypeptide comprises the enzymatically active portion of a protease.

19. The hybrid molecule of claim 4, wherein said polypeptide comprises the enzymatically active portion of a nuclease.

20. The hybrid molecule of claim 4, wherein said polypeptide comprises the enzymatically active portion of a toxin.

21. The hybrid molecule of claim 4, wherein the covalent bond connecting said second and third parts is a disulfide bond.

22. The hybrid molecule of claim 4, wherein the covalent bond connecting said second and third parts is a peptide bond or a proteolytically-sensitive disulfide loop.

23. The hybrid molecule of claim 8, wherein said naturally occurring protein of (b) is ricin.

24. The hybrid molecule of claim 11, wherein said hormone is selected from the group consisting of insulin, interleukin II, interleukin IV, interleukin VI and, epidermal growth factor (EGF).

25. The hybrid molecule of claim 14, wherein said toxin is, diphtheria toxin.

26. The hybrid molecule of claim 20, wherein said toxin is selected from the group consisting of cholera toxin, LT toxin, C3 toxin, Shiga toxin, Shiga-like toxin, ricin toxin, pertussis toxin, tetanus toxin, diphtheria toxin, and Pseudomonas exotoxin A.

27. The hybrid molecule of claim 22, wherein said first part is a polypeptide and the covalent bond connecting said first and second parts is a peptide bond.

28. The hybrid molecule of claim 24, wherein said hormone is interleukin II.

29. The hybrid molecule of claim 24, wherein said hormone is EGF.

30. The hybrid molecule of claim 26, wherein said toxin is cholera toxin.

31. The hybrid molecule of claim 26, wherein said toxin is Shiga-like toxin.

32. The hybrid molecule of claim 26, wherein said toxin is ricin toxin.

33. The hybrid molecule of claim 27, which is a recombinant protein.

34. A hybrid molecule comprising a first part, a second part and a third part connected by covalent bonds, (a) wherein said first part comprises a portion of the binding domain of a cell-binding polypeptide ligand effective to cause said hybrid protein to bind to a cell of an animal;

(b) wherein said second part comprises a portion of the translocation domain of diphtheria toxin which translocates said third part across the cytoplasmic membrane and into the cytosol of the cell; and (c) wherein said third part comprises a chemical entity to be introduced into the cell, wherein said chemical entity and said first part are non-native with respect to said diphtheria toxin, and further wherein said covalent bond connecting said second part and said third part is a cleavable bond.

35. The hybrid molecule of claim 34, wherein said first part comprises a portion of the binding domain of interleukin II effective to cause said hybrid molecule to bind to an interleukin II receptor-bearing cell.

36. The hybrid molecule of claim 34, wherein said first part comprises a portion of the binding domain of EGF.

37. The hybrid molecule of claim 34, wherein said second part comprises Fragment B' of diphtheria toxin illustrated in FIG. 3.

38. The hybrid molecule of claim 34, wherein said third part comprises the enzymatically active portion of cholera toxin.

39. The hybrid molecule of claim 34, wherein said third part comprises the enzymatically active portion of ricin toxin.

40. The hybrid molecule of claim 34, wherein said third part comprises the enzymatically active portion of Shiga-like toxin.

41. The hybrid molecule of claim 34, wherein the covalent bond connecting said second and third parts is a thioether bond.

42. The hybrid molecule of claim 32, wherein the covalent bond connecting said second and third parts is a disulfide bond.

43. The hybrid molecule of claim 34, wherein said third part is a polypeptide and the covalent bond connecting said second and third parts is a peptide bond or a proteolyticaily-sensitive disulfide loop.

44. The hybrid molecule of claim 43, wherein said first part is a polypeptide and the covalent bond connecting said first and second parts is a peptide bond.

45. The hybrid molecule of claim 44, which is a recombinant hybrid protein.

46. The hybrid molecule of claim 45, which is CTA/DTB'/IL2.

47. The hybrid molecule of claim 45, which is SLA/DTB'/IL2.

48. The hybrid molecule of claim 45, which is ricin A/DTB'/IL2.

49. A hybrid molecule comprising a first part, a second part, and a third part connected by covalent bonds, (a) wherein said first part comprises a portion of the binding domain of a cell-binding polypeptide ligand effective to cause said hybrid protein to bind to a cell of an animal;

(b) wherein said second part comprises a portion of a translocation domain of Shiga-like toxin which translocates said third part across the cytoplasmic membrane into the cytosol of the cell; and (c) wherein said third part comprises an enzymatically active domain of Shiga-like toxin.

50. The hybrid molecule of claim 49, wherein said cell-binding polypeptide ligand is interleukin-2.

51. The hybrid molecule of claim 49, wherein said covalent bond comprises a proteolytically sensitive disulfide loop.

* * * * *

UNITED STATES PATENT AND TRADEMARK OFFICE
CERTIFICATE OF CORRECTION

PATENT NO. : 6,022,950

DATED : February 8, 2000

INVENTOR(S) : Murphy

It is certified that error appears in the above-identified patent and that said Letters Patent is hereby corrected as shown below:

Column 2, line 6, "$cys_{461}$" (first occurrence) should read --$Cys_{461}$--.
Column 9, line 15, "The-endocytic" should read --The endocytic--.
Column 9, line 30, "$A_2$" should read --$A_1$--.
Column 19, line 56, cancel "comma" after the word "and".
Column 19, line 59, cancel "comma" after the word "is".
Column 20, line 50, "32" should read --34--.

Signed and Sealed this

Twenty-seventh Day of February, 2001

Attest:

NICHOLAS P. GODICI

*Attesting Officer* *Acting Director of the United States Patent and Trademark Office*